US007549424B2

(12) United States Patent
Desai

(10) Patent No.: US 7,549,424 B2
(45) Date of Patent: Jun. 23, 2009

(54) METHOD AND APPARATUS FOR TISSUE TREATMENT WITH LASER AND ELECTROMAGNETIC RADIATION

(75) Inventor: Ashvin Desai, San Jose, CA (US)

(73) Assignee: Pro Surg, Inc., San Jose, CA (US)

( * ) Notice: Subject to any disclaimer, the term of this patent is extended or adjusted under 35 U.S.C. 154(b) by 0 days.

(21) Appl. No.: 10/300,655

(22) Filed: Nov. 19, 2002

(65) Prior Publication Data

US 2003/0130575 A1    Jul. 10, 2003

Related U.S. Application Data

(63) Continuation-in-part of application No. 10/274,436, filed on Oct. 17, 2002, and a continuation-in-part of application No. 10/274,497, filed on Oct. 17, 2002, now abandoned, which is a continuation-in-part of application No. 10/193,721, filed on Jul. 10, 2002, which is a continuation-in-part of application No. 09/715,853, filed on Nov. 17, 2000, which is a continuation-in-part of application No. 09/510,537, filed on Feb. 22, 2000, now Pat. No. 6,461,296, which is a continuation-in-part of application No. 09/105,896, filed on Jun. 26, 1998, now Pat. No. 6,231,591, which is a continuation-in-part of application No. 08/639,199, filed on Apr. 26, 1996, now Pat. No. 5,861,002.

(60) Provisional application No. 60/383,015, filed on May 23, 2002.

(51) Int. Cl.
*A61B 19/00* (2006.01)
*A61F 7/00* (2006.01)

(52) U.S. Cl. ............................ 128/898; 606/14; 606/41; 607/101; 607/143; 604/21

(58) Field of Classification Search .................. 128/898; 606/2.4, 7, 14, 15, 23, 27, 32, 41–49; 607/88, 607/89, 96–101, 143; 604/20, 21, 48; 600/101
See application file for complete search history.

(56) References Cited

U.S. PATENT DOCUMENTS 557,589 A    7/1896 Lockwood ................... 251/349

(Continued)

FOREIGN PATENT DOCUMENTS

EP    327410    8/1989

(Continued)

*Primary Examiner*—Ahmed M Farah
(74) *Attorney, Agent, or Firm*—David H. Jaffer; Pillsbury Winthrop Shaw Pittman LLP

(57) ABSTRACT

A method and apparatus wherein an application of energy is limited to a specific diseased portion of body tissue (target tissue) for the purpose of localizing the treatment to the target tissue and avoiding an adverse effect on surrounding tissue. In one embodiment, access to the target tissue is provided by inserting an energy transmission device through a needle for delivery of the energy into the target tissue. Guidance of the needle is alternatively enhanced through use of an image guidance device. Alternatively, in addition the localized treatment is further controlled by use of an energy-concentrating/enhancement agent and/or photosensitizing/photoselective agent, chromophore dye and viscous substance to cause selective interaction with a specific wavelength of an energy source. The treatment can be further controlled and localized by improving the accuracy and positioning of the delivery device into the target tissue using imaging guidance.

3 Claims, 20 Drawing Sheets

U.S. PATENT DOCUMENTS

| | | | | |
|---|---|---|---|---|
| 1,314,855 A | | 9/1919 | Carpenter | 604/33 |
| 2,706,660 A | | 4/1955 | Johnson et al. | 251/348 |
| 3,605,744 A | | 9/1971 | Dwyer | 604/139 |
| 3,828,780 A | | 8/1974 | Morrison | 604/20 |
| 3,850,175 A | | 11/1974 | Iglesias | 606/46 |
| 3,948,259 A | | 4/1976 | Bolduc | 128/235 |
| 4,402,310 A | | 9/1983 | Kimura | 604/30 |
| 4,565,200 A | | 1/1986 | Cosman | 128/642 |
| 4,607,622 A | | 8/1986 | Fritch | 128/6 |
| 4,668,215 A | | 5/1987 | Allgood | 604/30 |
| 4,673,393 A | | 6/1987 | Suzuki et al. | 604/167 |
| 4,760,940 A | | 8/1988 | Wallace et al. | 251/354 |
| 4,776,840 A | | 10/1988 | Freitas | 604/33 |
| 4,895,565 A | | 1/1990 | Hillstead | 604/167 |
| 4,949,718 A | | 8/1990 | Neuwirth et al. | 128/401 |
| 4,950,267 A | * | 8/1990 | Ishihara et al. | 606/12 |
| 5,007,908 A | | 4/1991 | Rydell | 606/47 |
| 5,069,223 A | | 12/1991 | McRae | 128/734 |
| 5,071,419 A | | 12/1991 | Rydell et al. | 604/35 |
| 5,073,166 A | | 12/1991 | Parks | 604/105 |
| 5,084,044 A | | 1/1992 | Quint | 606/27 |
| 5,105,808 A | | 4/1992 | Neuwirth et al. | 128/401 |
| 5,123,902 A | * | 6/1992 | Muller et al. | 604/21 |
| 5,125,910 A | | 6/1992 | Freitas | 604/249 |
| 5,144,961 A | | 9/1992 | Chen et al. | 608/139 |
| 5,169,396 A | * | 12/1992 | Dowlatshahi et al. | 606/15 |
| 5,186,714 A | * | 2/1993 | Boudreault et al. | 604/21 |
| 5,188,591 A | | 2/1993 | Dorsey, III | 604/249 |
| 5,190,541 A | | 3/1993 | Abele et al. | 604/35 |
| 5,195,958 A | | 3/1993 | Phillips | 604/33 |
| 5,197,963 A | | 3/1993 | Parins | 606/41 |
| 5,219,348 A | | 6/1993 | Buess et al. | 606/40 |
| 5,230,704 A | | 7/1993 | Moberg et al. | 604/35 |
| 5,244,459 A | | 9/1993 | Hill | 604/249 |
| 5,247,966 A | | 9/1993 | Stevens et al. | 604/249 |
| 5,273,524 A | | 12/1993 | Fox et al. | 604/21 |
| 5,281,218 A | | 1/1994 | Imran | 606/41 |
| 5,295,956 A | | 3/1994 | Bales et al. | 604/35 |
| 5,312,399 A | * | 5/1994 | Hakky et al. | 606/15 |
| 5,347,990 A | | 9/1994 | Ebling | 606/139 |
| 5,370,675 A | * | 12/1994 | Edwards et al. | 607/101 |
| 5,385,544 A | | 1/1995 | Edwards et al. | 604/22 |
| 5,456,661 A | * | 10/1995 | Narciso, Jr. | 604/20 |
| 5,460,628 A | | 10/1995 | Neuwirth et al. | 606/28 |
| 5,472,441 A | * | 12/1995 | Edwards et al. | 606/41 |
| 5,514,669 A | * | 5/1996 | Selman | 514/63 |
| 5,562,703 A | * | 10/1996 | Desai | 606/210 |
| 5,653,692 A | | 8/1997 | Masterson et al. | 604/113 |
| 5,672,171 A | * | 9/1997 | Andrus et al. | 606/15 |
| 5,931,834 A | * | 8/1999 | Murphy-Chutorian et al. | 606/7 |
| 6,461,296 B1 | * | 10/2002 | Desai | 600/210 |
| 6,558,382 B2 | * | 5/2003 | Jahns et al. | 606/41 |

FOREIGN PATENT DOCUMENTS

WO     WO94/04220     3/1994

\* cited by examiner

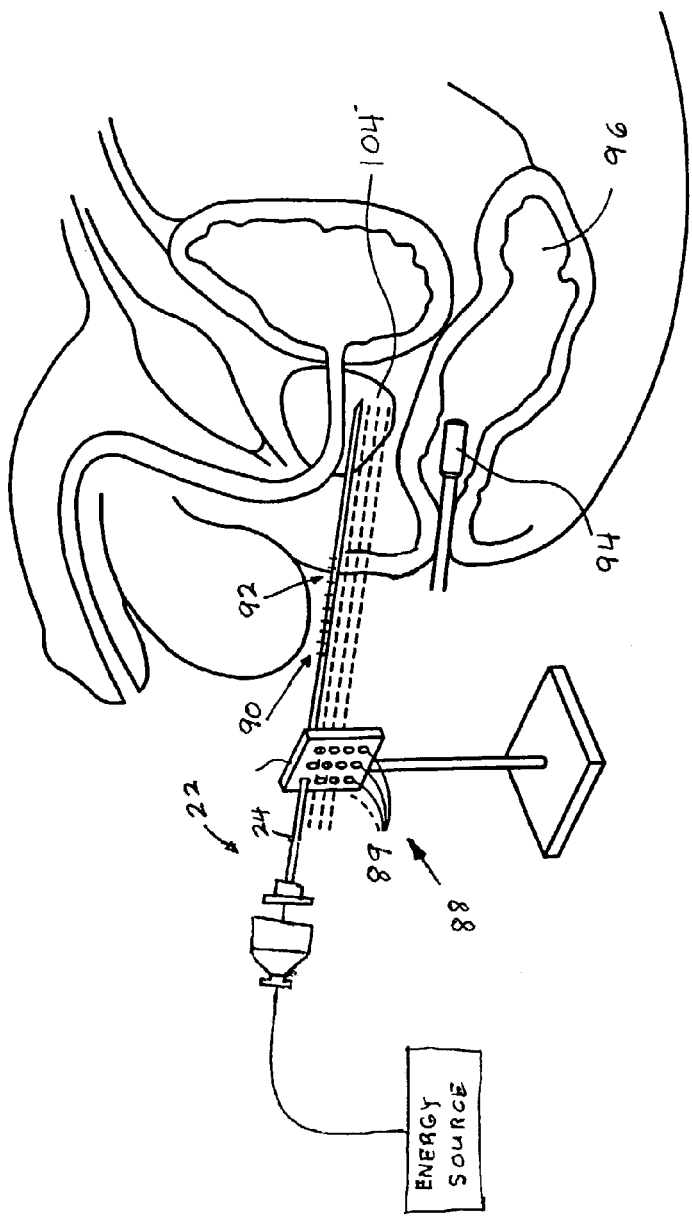
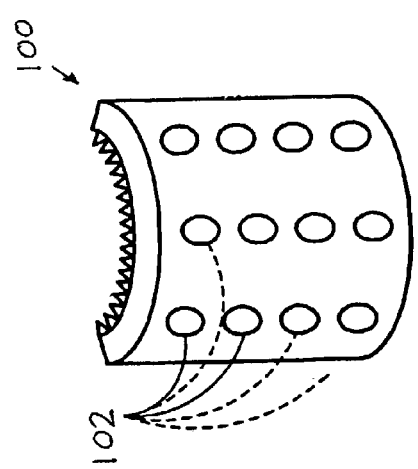
FIG. 5

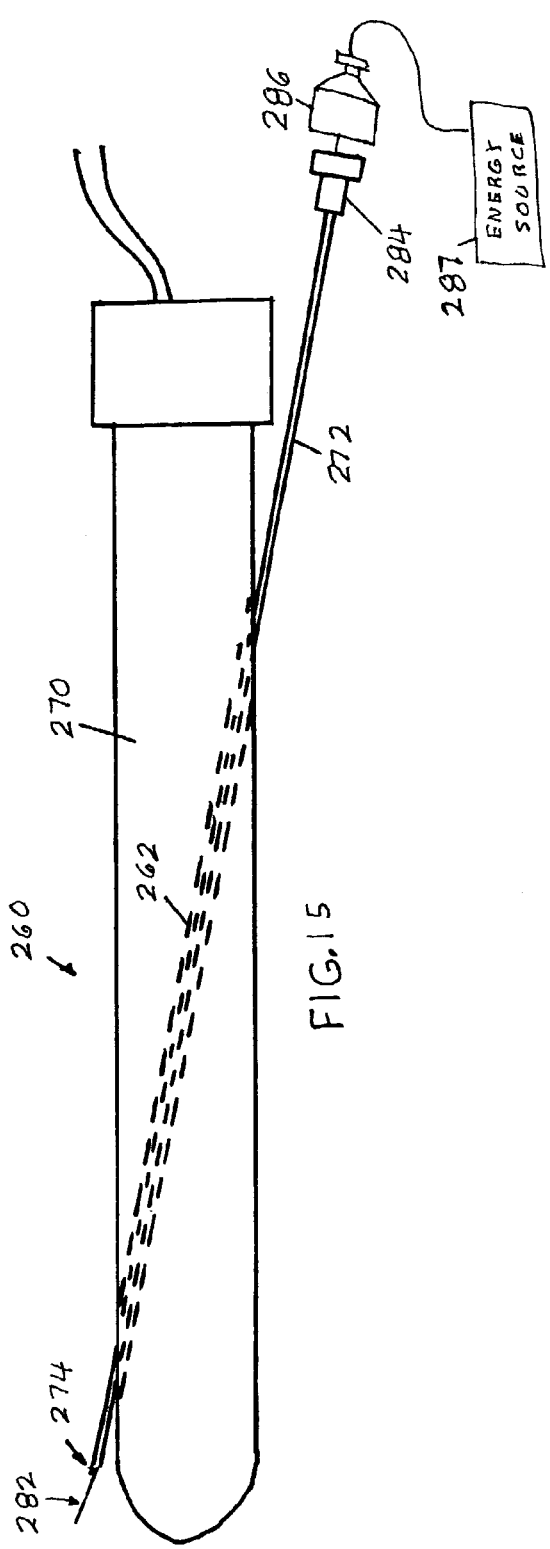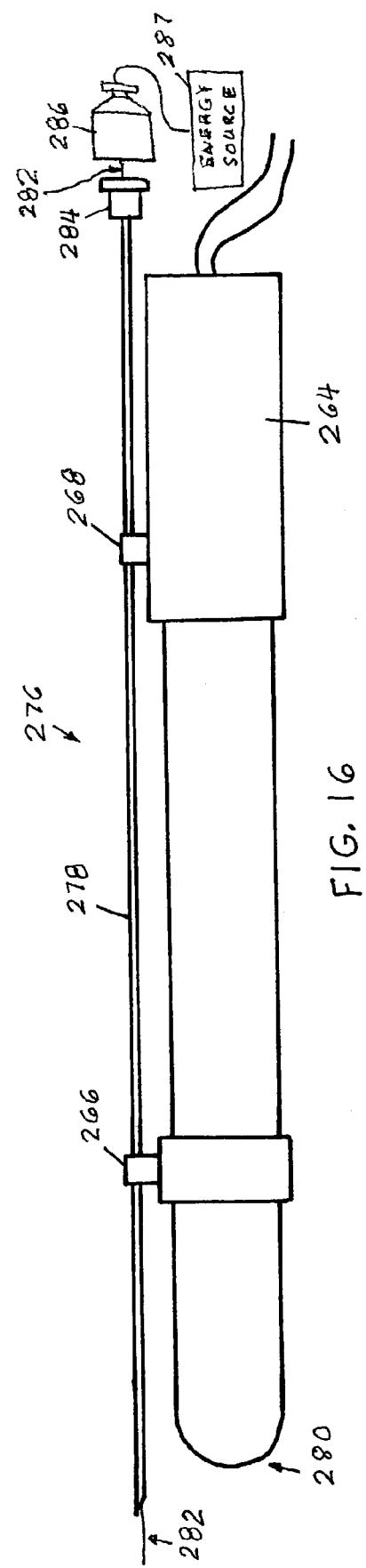

METHOD AND APPARATUS FOR TISSUE TREATMENT WITH LASER AND ELECTROMAGNETIC RADIATION

RELATED CASES

This application is a continuation in part of each of U.S. patent application Ser. Nos. 10/274,436 and 10/274,497, now abandoned both filed Oct. 17, 2002 and both of which are continuations-in-part of U.S. patent application Ser. No. 10/193,721 filed on Jul. 10, 2002 (which claims priority from U.S. Provisional Application 60/383,015 filed May 23, 2002). which is a continuation-in-part of U.S. patent application Ser. No. 09/715,853 filed Nov. 17, 2000, which is a continuation-in-part of U.S. patent application U.S. patent application Ser. No. 09/510,537 filed Feb. 22, 2000 (now U.S. Pat. No. 6,461,296), which is a continuation-in-part of U.S. patent application Ser. No. 09/105,896 filed Jun. 26, 1998 (U.S. Pat. No. 6,231,591), which is a continuation-in-part of U.S. patent application Ser. No. 08/639,199 filed Apr. 26, 1996 (U.S. Pat. No. 5,861,002) The contents of each of these applications is incorporated in this application by reference.

BACKGROUND OF THE INVENTION

1. Field of the Invention

The present invention relates generally to methods and apparatus for body tissue treatment using laser energy and electromagnetic radiation, and more specifically to methods and apparatus wherein laser energy and electromagnetic radiation are delivered to target tissue for controlled heating of tissue and for enhancing localized tissue necrosis. The thermal energy can be generated from Laser, microwave, electromagnetic radiation, RF and ultrasound or combinations of energy sources.

2. Description of the Prior Art

Various methods of treating diseased body tissue have been employed, including surgical removal, freezing, heating, chemical treatment, RF and Laser radiation. A variety of treatment methods and energy delivery approaches to target tissue are also known to be useful in treating diseased tissue. For example, various types of energy sources have been used including RF, microwave, and laser radiation to deliver energy to a body organ to cause tissue necrosis. The current methods of delivery of energy from these sources in the form of electromagnetic radiation is to apply them externally to target tissue to cause tissue necrosis. The result is uncontrolled tissue destruction, including healthy tissue surrounding a diseased part. In many cases, it would be advantageous to be able to only treat a localized target tissue of a body organ by applying electromagnetic radiation energy directly into the target tissue to cause localized tissue necrosis.

The treatment of diseased tissue is aided by use of endoscopic surgical instruments that allow a surgeon to see inside the body organ of a patient without the necessity of making large incisions. Although endoscopic surgical instruments have been developed and are in use for surgical operations, an apparatus and method for delivery of laser and electromagnetic radiation percutaneously, under "Real Time" imaging guidance in to precise target tissue of a body organ is not described or used in the prior art.

It is therefore apparent that there is a need for an improved method for treating diseased tissue including an apparatus that can deliver a controlled amount of electromagnetic energy into target tissue located within the interior of a body organ. There is also a need for a method providing greater control, ease of operation and "Real Time" imaging guidance for endoscopic treatment of target tissue during a surgical procedure.

SUMMARY

It is therefore an object of the present invention to provide an improved method of treating a localized volume of body tissue;

It is a further object of the present invention to provide a method of tissue treatment by delivering laser energy and/or electromagnetic radiation directly in to target tissue;

It is another object of the present invention to provide a method of tissue treatment including injection of radiation activating/enhancing agents and photoselective/photosensitive agents and viscous substances to cause controlled necrosis of target tissue from selective absorption of laser energy and/or electromagnetic radiation to cause controlled and selective tissue necrosis;

It is another object of the present invention to provide a method of tissue treatment including injection of an energy enhancement substance to enhance the effect of application of laser energy and/or electromagnetic radiation;

It is another object of present invention to provide a composition and formulation for energy activating agents, viscous photosensitizing substance, and enhancement substances for use with application of laser energy and electromagnetic radiation;

It is a still further object of the present invention to provide a method of body tissue treatment wherein a laser energy and/or electromagnetic radiation delivery fiberoptics or waveguide is inserted through a needle in to target tissue percutaneously, transperineally, transrectally, transvaginally, transurethrally, laparoscopically and by other endoscopic approaches through a natural body opening or an incision in the skin under visual or non-invasive imaging guidance including CT, MRI, Ultrasound, x-ray, gamma rays and other imaging modalities;

It is a still further object of the present invention to provide a method of body tissue treatment wherein a laser energy and/or electromagnetic radiation delivery fiberoptics or waveguide is inserted directly in to target tissue by any of various ways including percutaneously, transperineally, transrectally, transvaginally, transurethrally, laparoscopically and by other endoscopic approaches through a natural body opening or an incision in the skin under visual or non-invasive imaging guidance including CT, MRI, Ultrasound, x-ray, gamma rays and other imaging modalities;

It is an object of the present invention to deliver laser energy and electromagnetic radiation through a working channel or needle guide mounted on a selected imaging device including a cystoscope, laparoscope, hysteroscope, gastroscope, resectoscope, transrectal ultrasound imaging probe, transvaginal ultrasound probe, laparoscopic ultrasound probe, intraluminal or ultrasound imaging probe and other rigid, semi-rigid and flexible endoscopes, imaging probes and devices.

It is an object of the present invention to provide a method of body tissue treatment, wherein laser energy and electromagnetic radiation can be delivered directly in to target tissue through use of a device selected from the group consisting of a needle guide, grid, template positioning instrument, biopsy needle, biopsy needle guide, endoscopic instrument, finger guide, access probe, trocar assembly and image guiding device.

It is another object of the present invention to provide a method of delivering a specific laser energy wavelength and/ or electromagnetic radiation spectrum/wavelength and energy density for a specified treatment time to a specific, localized limited interior portion of a body organ for treatment.

It is a further object of the present invention to provide a method of delivering laser energy and/or electromagnetic radiation to a specific, localized portion/target tissue by using a device inserted from the group consisting of a needle guiding device, fiberoptics, waveguide or other energy delivery apparatus under guidance of a non-invasive imaging device including CT, MRI, X-Ray, gamma ray apparatus and other non-invasive apparatus.

Briefly, a preferred embodiment of the present invention includes a method and apparatus wherein an application of laser and/or electromagnetic radiation energy is limited to a specific diseased portion of body tissue (target tissue) for the purpose of localizing the treatment to the target tissue and avoiding an adverse effect on surrounding tissue. In one embodiment, access to the target tissue is provided by inserting a needle. An energy transmission device is then inserted through the needle for delivery of the energy into the target tissue. Guidance of the needle is alternatively enhanced through use of an image guidance device. Alternatively, in addition the localized treatment is further controlled by use of an energy-concentrating/enhancement agent including a photosensitizing/photoselective agent and a viscous substance to cause selective interaction with a specific wavelength of an energy source. The treatment can be further controlled and localized by improving the accuracy and positioning of the delivery device into the target tissue using imaging guidance.

An advantage of the present invention is that it allows the controlled delivery of laser and electromagnetic radiation energy to target tissue in a localized manner without affecting the surrounding healthy tissue.

A further advantage of the present invention is that it provides a selective treatment of diseased tissue such as malignant cancer cells, avoiding the need to expose a large portion of a patient's body to toxic radiation.

A still further advantage of the present invention is that application of laser energy and/or other energy types can be easily and safely delivered to target tissue by way of access methods such as percutaneous, transrectal, transperineal, laparoscopic, transvaginal and other approaches directly into a target organ/tissue under imaging and instrumental guidance.

IN THE DRAWING

FIG. 5 shows use of a grid to guide placement of a needle for use in installing a delivery device for local application of energy to a body part;

FIG. 15 shows an ultrasound probe device with an internal needle guide for guiding a needle to target tissue for installation of a transmission device for a localized application of energy;

FIG. 16 shows an ultrasound probe with an external needle guide for use in inserting a needle into a target tissue for installation of a transmission device for local application of energy;

DETAILED DESCRIPTION OF THE PREFERRED EMBODIMENT

Figure 1:
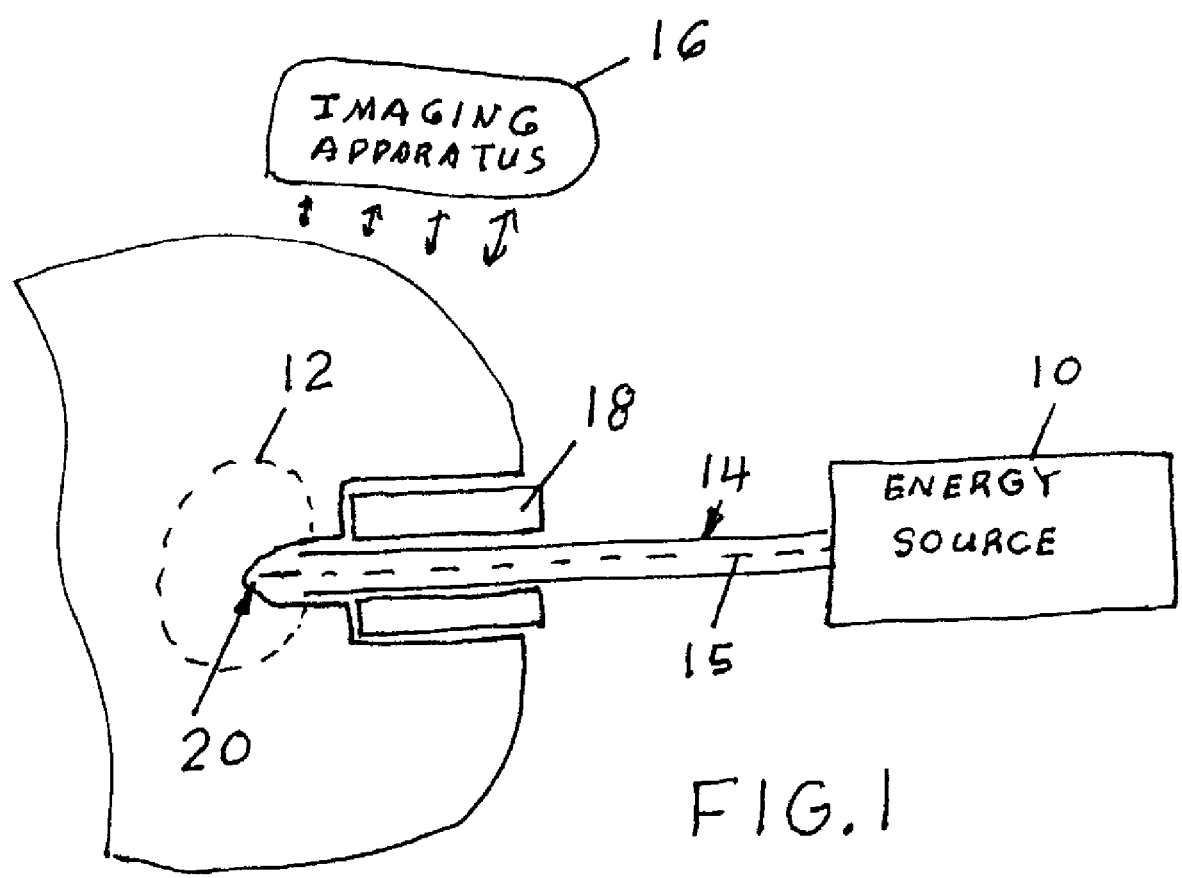
FIG. 1 is a generalized illustration of localized energy application according to the present invention.

The present invention is illustrated in the symbolic diagram of FIG. 1 wherein an energy source 10 supplies any of a variety of energy types including laser energy and/or other electromagnetic energy that is transmitted to a target tissue 12 through a transmission device 15. The transmission device is preferably constructed as a device that serves to carry energy from the source to the target tissue without radiating energy along the path. Examples of these types of transmission devices will be given in reference to FIGS. 3A-3C of the drawing. Item 14 in FIG. 1 represents a delivery apparatus that includes the transmission device symbolized by dashed line 15. In one embodiment (FIG. 3C), the delivery apparatus is physically the same as the transmission device. In other embodiments, for example see FIGS. 3B and 3C, the delivery apparatus includes a hollow core needle with a transmission device enclosed within the needle, all for the purpose of delivering the energy. In alternate embodiments the needle is also for delivery of a substance for enhancing local application of the energy. Guidance apparatus is illustrated, again symbolically, by item 16 representing non-invasive apparatus and item 18 representing invasive guidance apparatus.

The method of use of the apparatus of FIG. 1 includes inserting the delivery apparatus 14 into the body to the target tissue 12, and then delivering energy from the supply 10 through the transmission device 15 to the target tissue 12. Alternatively, guidance apparatus 16 and/or 18 may be used to assist in positioning the apparatus 14, and in extending the end 20 of the transmission device 15 as required in the target tissue 12.

The present invention focuses on use of a transmission device for applying a selected laser and/or other electromagnetic energy form to a selected, localized portion (target tissue) of a body interior. The following detailed descriptions will illustrate various types of delivery apparatus, and various ways of inserting a transmission device into a body and achieving a localized energy application. In summary, a delivery apparatus can be inserted percutaneously and interstitially or through an incision, or through a natural body opening. The present invention also includes various apparatus configured for use in inserting the transmission device, and non-invasive and invasive guidance apparatus. Non-invasive apparatus includes templates, and imaging devices positioned outside the body for observing the delivery apparatus as it is positioned in a body. Non-invasive imaging apparatus includes ultrasound, CT, MRI, x-ray, and gamma ray apparatus. Invasive guiding apparatus includes hollow core needles, biopsy needle apparatus, and various channels of invasive apparatus such as endoscopic instruments, catheters, and probes including for example an ultrasound probe. Many different kinds of scopes can be used, including a laparoscope, cystoscope, resectoscope, hysteroscope, gastroscope, bronchoscope, and uteroscope.

In addition to inserting a transmission device, the localization of energy is further enhanced according to the present invention through injection of a substance that is absorbed more readily by tumor tissue than by healthy tissue, and wherein the substance provides a path for applied energy that draws the energy and therefore further confines it to the diseased target tissue.

The present invention also includes various transmission device distal end tip configurations which will be described in detail in the following, for achieving a desired radiation pattern of the transmitted energy for optimum distribution of the energy throughout the target tissue. The above-summarized elements of the method and apparatus of the present invention will now be illustrated in the following text in reference to the figures of the drawing.

Figure 2:
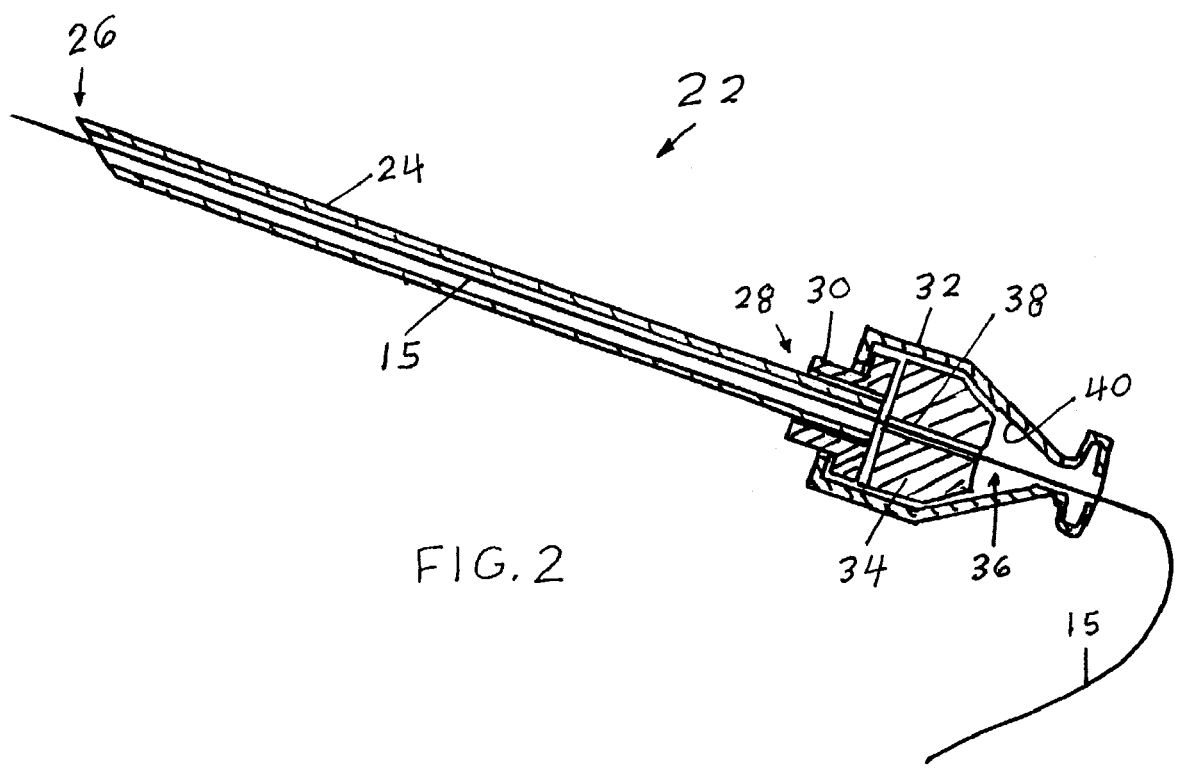
FIG. 2 shows a needle and apparatus for locking a transmission device in position upon installation through the needle.

FIG. 2 illustrates the use of a needle apparatus 22 for use in percutaneously and/or interstitially accessing a target tissue. The apparatus 22 includes a hollow core needle 24 with distal end 26 configured for penetrating tissue, and a proximal end 28 with a connector 30 attached for connection with a locking cap 32 apparatus. The locking cap apparatus 32 includes a flexible ring bushing 34 apparatus in the cap interior. The dimensions of the flexible bushing 34 and interior 36 are designed so as to allow free movement/passage of the transmission device 15 through the bushing 34 hole 38 with the cap 32 disconnected from the connector 30. The interior 36 is further designed so that upon connecting the cap 32 with the connector 30, the bushing is compressed, causing the hole 38 in the bushing 34 to slightly close and provide a friction fit with the transmission device 15 for holding it in place. For example, as shown in FIG. 2, the back interior wall 40 is tapered, and when the bushing 34 is pressed against it from the pressure of mating the bushing with the connector, the force causes the cavity hole 38 to collapse and press against the transmission device 15. Although a locking cap 32 and connector 30 are shown as apparatus for securing a transmission device, many other types of apparatus can be configured/designed to perform the function of securing the transmission device, as will be apparent to those skilled in the art. These various apparatus are also included in the spirit of the present invention.

Figure 3A:
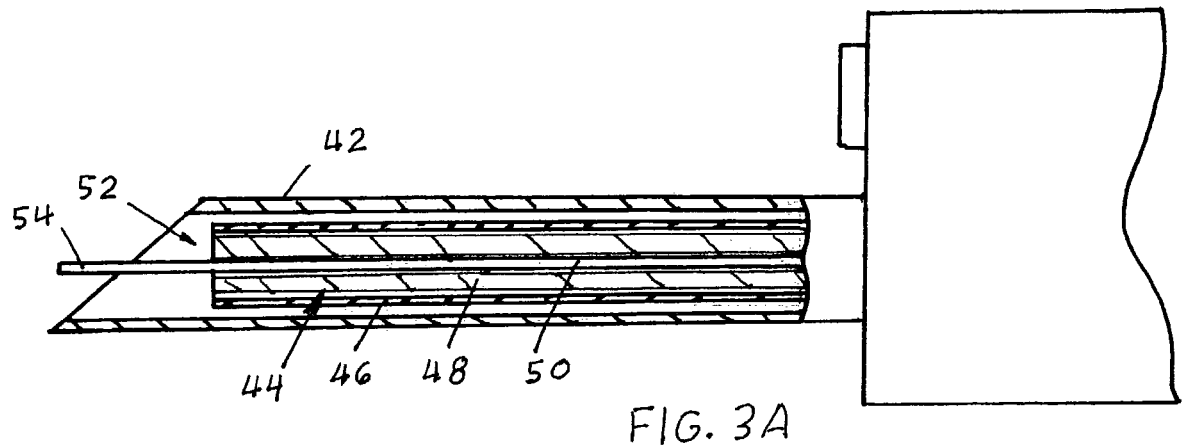
FIG. 3a illustrates use of TEM mode cable for delivery of energy.
Figure 3B:
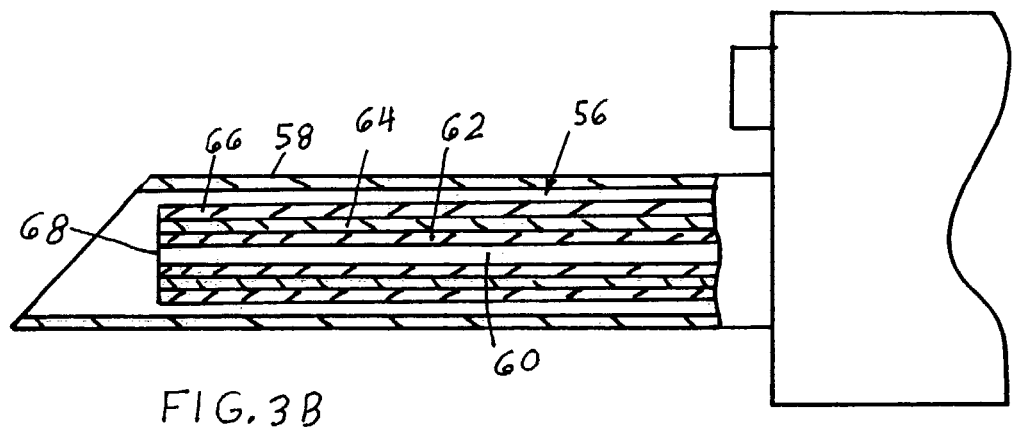
FIG. 3b shows use of a typical optics cable for delivery of energy.
Figure 3C:
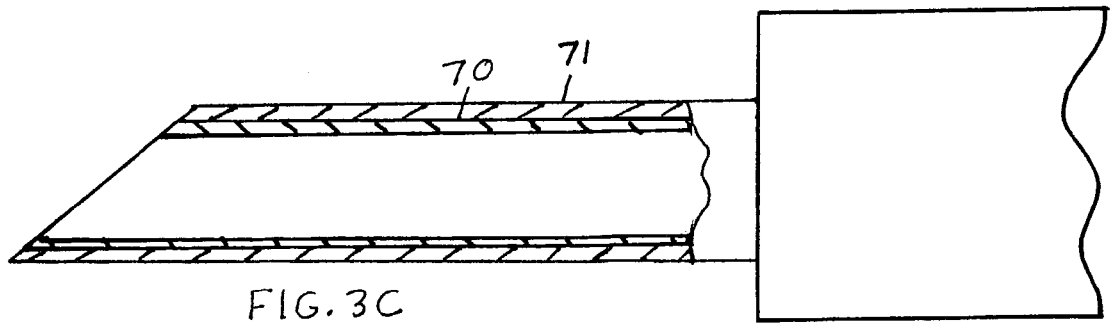
FIG. 3c illustrates use of a hollow waveguide for use as an energy delivery device.

FIGS. 3A-3C illustrate examples of transmission devices and their insertion/installation in a needle. FIG. 3A shows a hollow core needle 42 in which is installed a coaxial transmission device 44 that can propagate in a TEM (transverse electromagnetic) mode for a broad frequency range of electromagnetic energy. The line has a tubular outer conductor 46, a tubular insulator 48, and center conductor 50. The radiation pattern from the distal end 52 into the diseased tissue can be controlled by configuring an antenna which, for example, can simply be an extension 54 of the center conductor 50, or it can be a formation of a loop, or other configuration or attachment.

FIG. 3B illustrates a fiber optic cable 56 in a hollow core needle 58. A typical fiber optic cable 56 for example has a core 60 surrounded by a cladding 62 of hard polymer, which is covered by a buffer 64 and then a Teflon jacket 66. The distal end 68 of the core 60 can be configured for optimum dispersion/radiation of energy, for example in a dome or tapered shape. FIG. 3C shows a needle 70 with inside dimensions designed for use as a waveguide for electromagnetic energy. The shape of the interior can be round, such as for transmission in a $TE_{111}$ mode, or it can be rectangles for a $TE_{01}$ mode rectangular waveguide commonly used in microwave transmission.

The present invention also includes transmission devices, and needles and probes in which a transmission device is enclosed, that are constructed from heat insulated materials. In practice of the present invention, the transmission device is usually inserted directly into the target tissue or a energy conductive substance for passing the energy to the target tissue i.e., the transmission device is in thermal contact with the target tissue. As the energy from the transmission device is emitted, the temperature of the target tissue and conductive substance rises. A transmission device or probe or i.e., delivery device in contact with the conductive substance or target tissue will conduct the heat according to its thermal conductivity. As a result, the tissue through which the transmission device passes will also rise in temperature and be subject to damage. This is generally an undesirable result. In order to minimize or avoid this problem, the transmission device can, as an alternate embodiment, be coated with a thermally insulating material, or in some cases constructed of thermally insulative material. For example, light energy can be transmitted through a fiberoptic core of lesser thermal conductivity than a metal, and the fiberoptic can alternatively be in addition coated with insulative materials, which for illustration could be coating 66 in FIG. 3B. A transmission device having a metal outer conductor, such as guide 70 of FIG. 3C, or the outer conductor 46 of FIG. 3A can be covered with a thermally insulating material, such as 71 in FIG. 3C. In FIG. 3A, the needle 42 can be constructed of a heat insulative material. Examples of insulative materials are quartz, ceramic, polymers, co-polymers and composite materials.

Figure 4A:
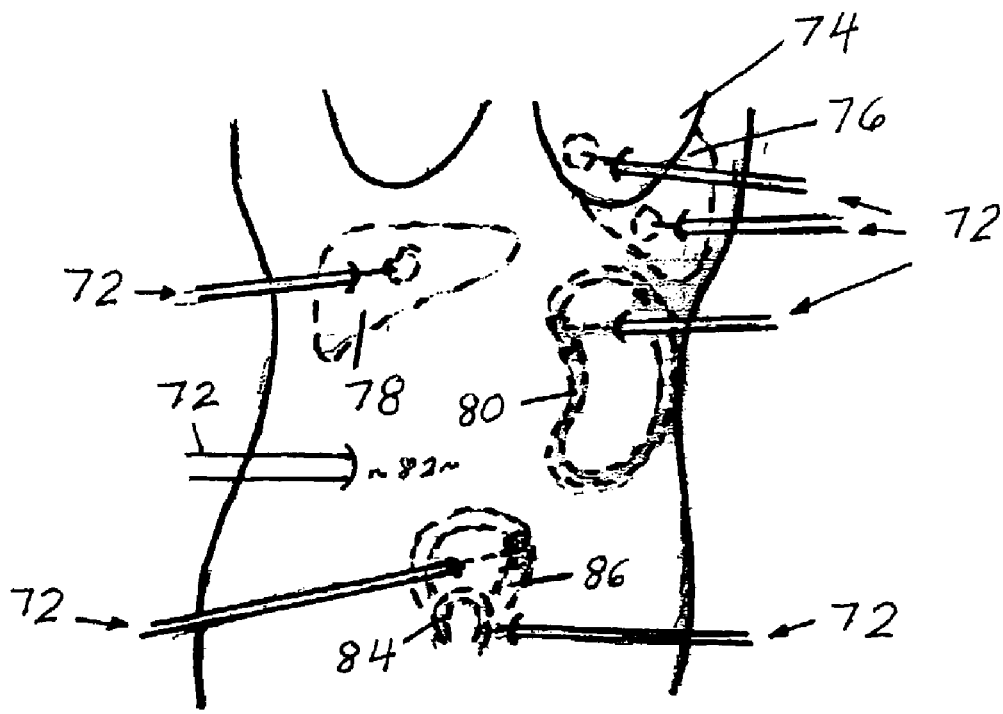
FIG. 4A illustrates access to various body parts for achieving localized energy application.
Figure 4B:
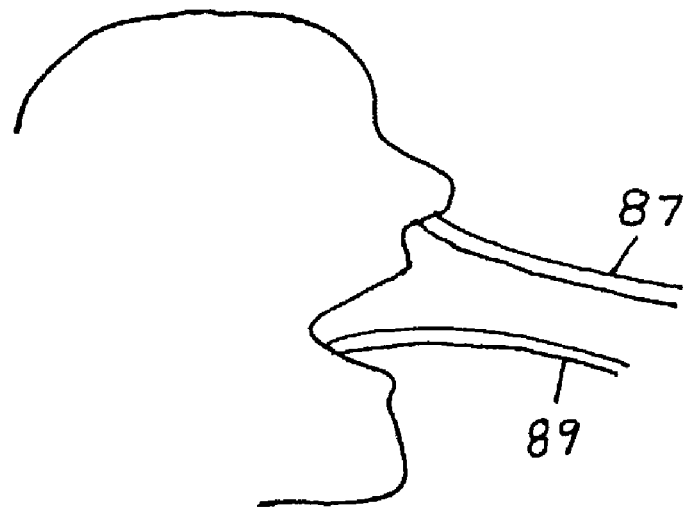
FIG. 4B illustrates access to an interior body part through the nose and/or mouth.

FIG. 4A is presented to clarify that the method of the present invention applies to any body part. FIG. 4A shows various organs being accessed by undefined devices 72 representing any of the apparatus presented in the present disclosure for the purpose of access to a target tissue. FIG. 4, for example, shows access to a breast 74, lung 76, liver 78, kidney 80, abdominal cavity 82, bladder 84 and uterus 86. Access can be through an incision, or via any natural body opening. FIG. 4B illustrates the use of the apparatus of the present invention for access to interior body parts through the nose and mouth opening with probe(s) 87, 89. A more detailed description of an applicable apparatus with a flexible probe for access is illustrated in reference to FIG. 8.

FIG. 5 shows an external guidance apparatus in the form of a positioning grid apparatus 88 with a plurality of holes 89 for positioning and guiding a needle apparatus such as apparatus 22 of FIG. 2. The depth of penetration of the needle can be accounted for with depth indicating marks 90 on the needle 24 observed relative to the apparatus 88 or an insertion point 92 on the body. FIG. 5 also illustrates the use of ultrasound imaging in guiding the placement of the needle by placing an ultrasound probe 94 in the rectum 96. The positioning grid apparatus 88 can also be in a flexible form 100. The grid/plurality of holes 102 in form 100 or holes in apparatus 88 are for guiding needle placement transperineally in a plurality of positions for localized treatment of a prostate 104. A similar positioning grid can be used for guiding needle placement in other organs including breast, liver, kidney, brain and lungs.

Figure 14:
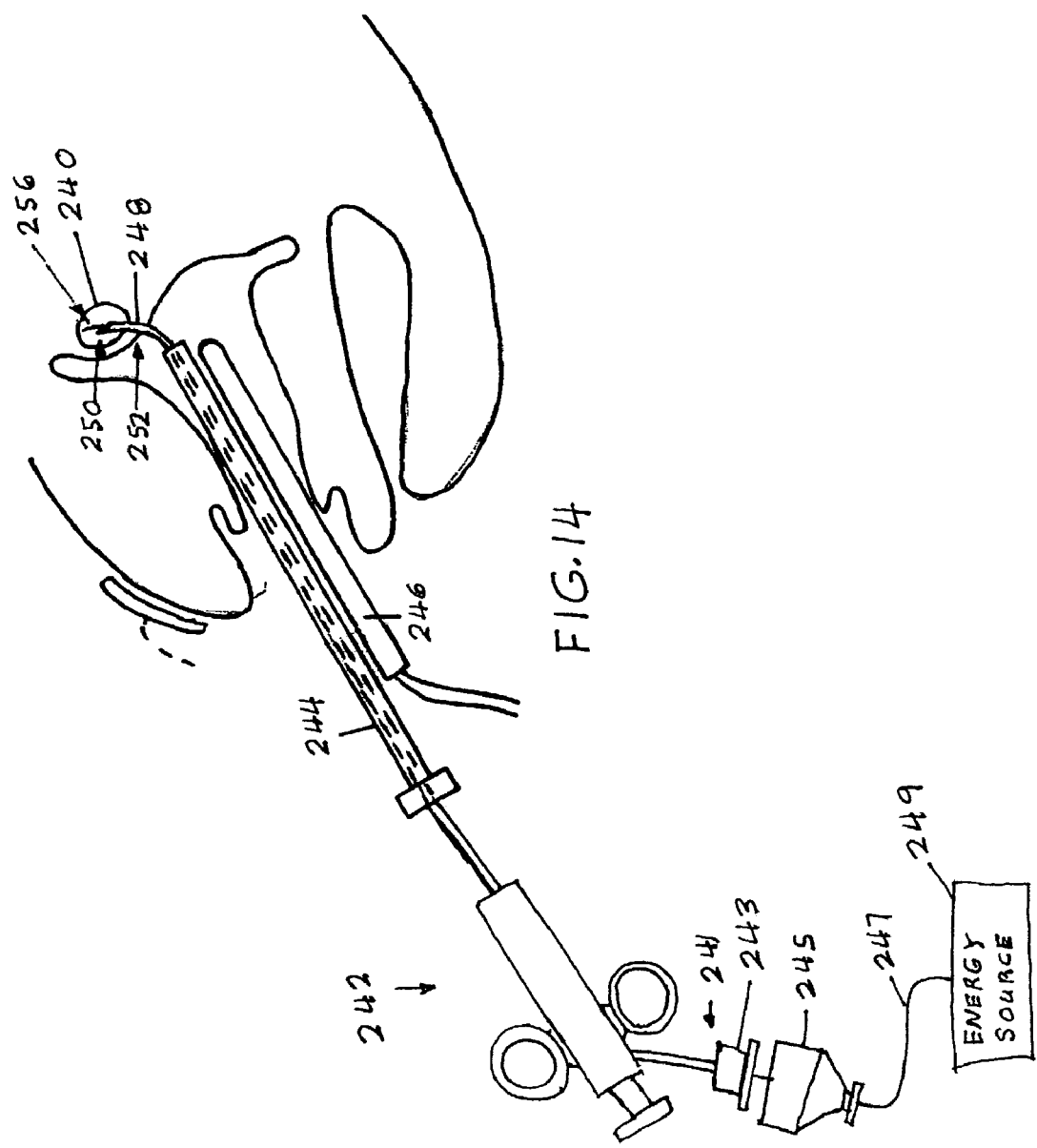
FIG. 14 illustrates transvaginal access to a uterus using a biopsy device for inserting a needle into a target tissue for installation of a transmission device therethrough for a localized application of energy.

The needle apparatus 22 as shown in FIG. 5 is for insertion of a transmission device as explained above, and as shown in FIG. 5 for treatment of a prostate with laser and electromagnetic energy. The needle can also be used for injection of a treatment substance. The apparatus of FIG. 5 is also shown in FIG. 14 of U.S. patent application Ser. No. 10/193,721, except for the application of a transmission device as described herein.

The apparatus shown in FIGS. 6-16 of the present application are generally described for use in accessing a target tissue for injection of a treatment substance through a needle. These descriptions apply generally in explanation of the present invention. The primary difference is that the apparatus as applied to the present invention is for installation of a transmission device through a needle. Injection of a substance through the needle is also included in the present invention in combination with the application of energy, including laser and electromagnetic energy, through a transmission device.

FIGS. 6-16 as shown herein differ from the corresponding figures in the related cases, the contents of which are incorporated by reference, in that the insertion of a transmission device is shown in the present invention instead of only showing the injection of a treatment substance. The related cases also show a method of applying RF energy, which differs from the method of applying energy disclosed in the present invention producing non-radiating lines of various types.

Figure 6:
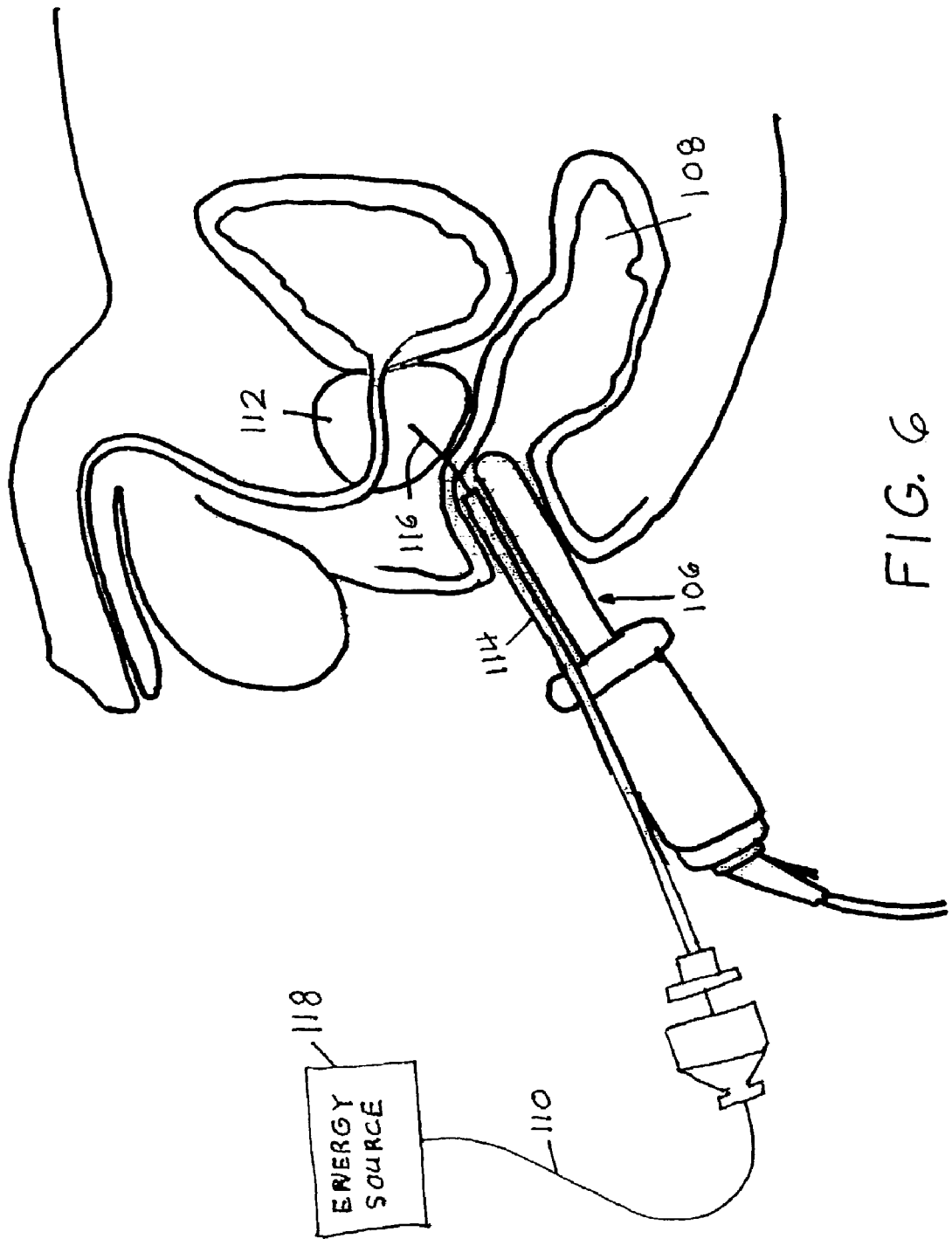
FIG. 6 illustrates accessing a prostrate through the rectum, using a rectal ultrasound probe to guide placement of a needle for use in inserting a transmission device for local application of energy.

FIG. 6 shows use of an invasive ultrasound probe 106 inserted in a rectum 108 for use in providing an ultrasound image for guiding the installation of a transmission device 110 into a prostate 112. In this illustration, a biopsy needle guide 114 is used to aid in insertion of a needle 116 in which the transmission device is inserted. FIG. 6 shows an energy source 118. Apparatus similar to that of FIG. 6 is further described in FIG. 15 of U.S. patent application Ser. No. 10/193,721 incorporated by reference, as applied for injection of a treatment substance.

Figure 10:
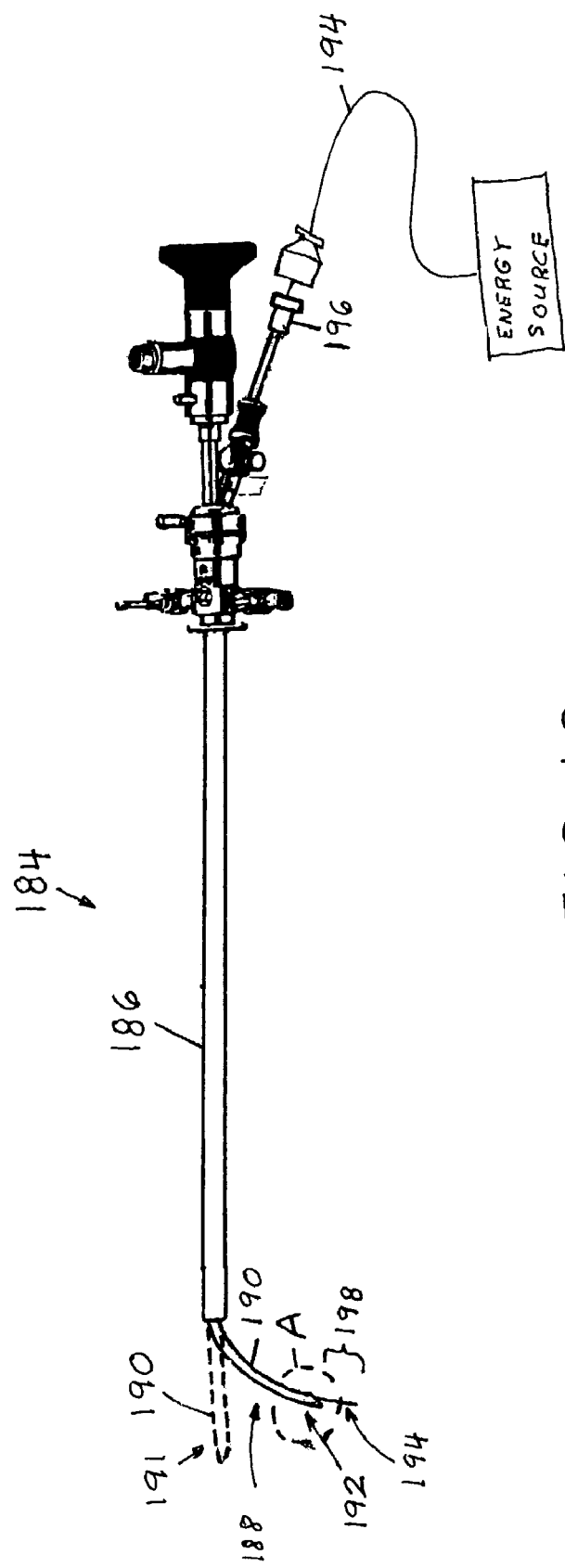
FIG. 10 is an endoscopic apparatus configured for installation of a needle through which a transmission device is inserted for application of energy to a target tissue.

FIG. 7A shows use of non-invasive guidance with an imaging device 120 for direct percutaneous and interstitial insertion of a needle 122 into a target tissue 124 for installation of a transmission device 125 through the needle 122 for transmission of energy from a source 127 to tissue 124. FIG. 7A also shows use of an endoscope 126 for installation of a needle 128 into a target tissue 130 by way of an opening 132 which for purposes of illustration can be either a natural body opening or a surgically prepared opening. A transmission device 134 for connection to an energy source 135 is fed into the needle apparatus 136 through an opening through the connector 140, and when the transmission device is correctly positioned, the locking cap 32 is secured on the connector 140 to secure the transmission device position, as explained in reference to FIG. 2. The construction of an endoscope such as 126 is given in more detail in the incorporated text of the related cases. FIG. 10 of U.S. patent Ser. No. 10/195,721 is similar to FIG. 7A herein, and can be referred to, as well as other references in the related cases incorporated by reference, for additional explanation of the apparatus 126. It should be noted, however, that the RF application apparatus as described in U.S. patent Ser. No. 10/195,721 is not needed in the apparatus and method of the present disclosure. Referring to FIG. 7A of the present disclosure, in accessing the target tissue 130 with use of the endoscope 126, the non-invasive imaging 120 can also be used to aid placement as an alternative embodiment. FIG. 7B is used herein to illustrate that a channel 129 of an endoscope 131 such as 126 can be used for irrigation of a body interior, and for evacuation along with the injection of photosensitizing substances, dyes, and agents. Item 133, for example, can symbolize an injection device for injection of a fluid in liquid, solid, semi-solid, suspension, conjugate or viscous form. Item 133 for illustration also represents a pump for evacuation. It also is to be understood that a separate line or lines can be inserted for irrigation and evacuation. Various apparatus and methods of irrigation and evacuation will be apparent to those skilled in the art, and these are included in the present invention in combination with the application of energy and substances described herein.

Figure 7:
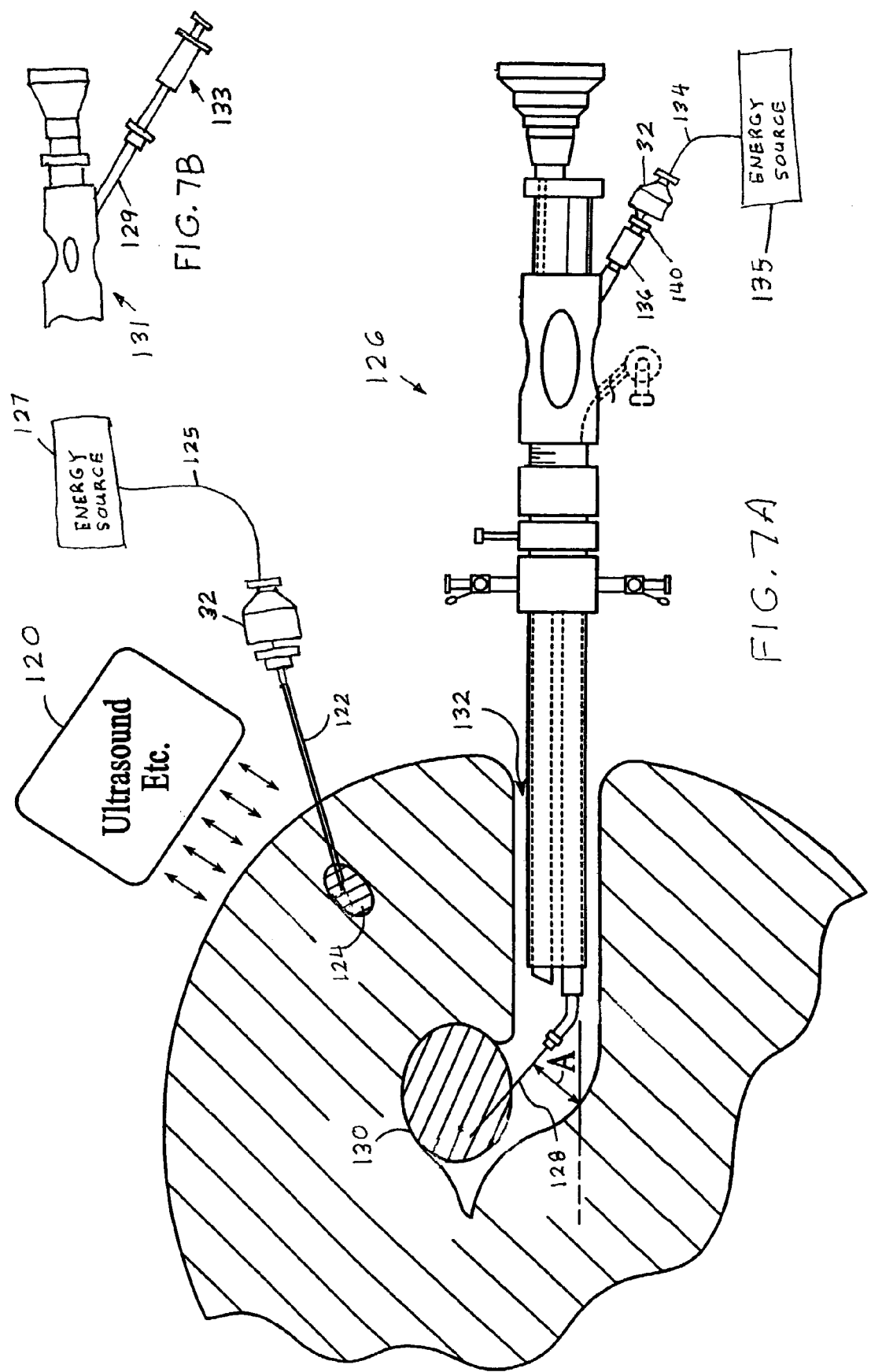
FIG. 7A illustrates percutaneous needle access, with non-invasive ultrasound guidance, and access to target tissue or using an endoscopic instrument for placement of a needle for installation of a transmission device through the needle.
FIG. 7B illustrates irrigation and aspiration.
Figure 8:
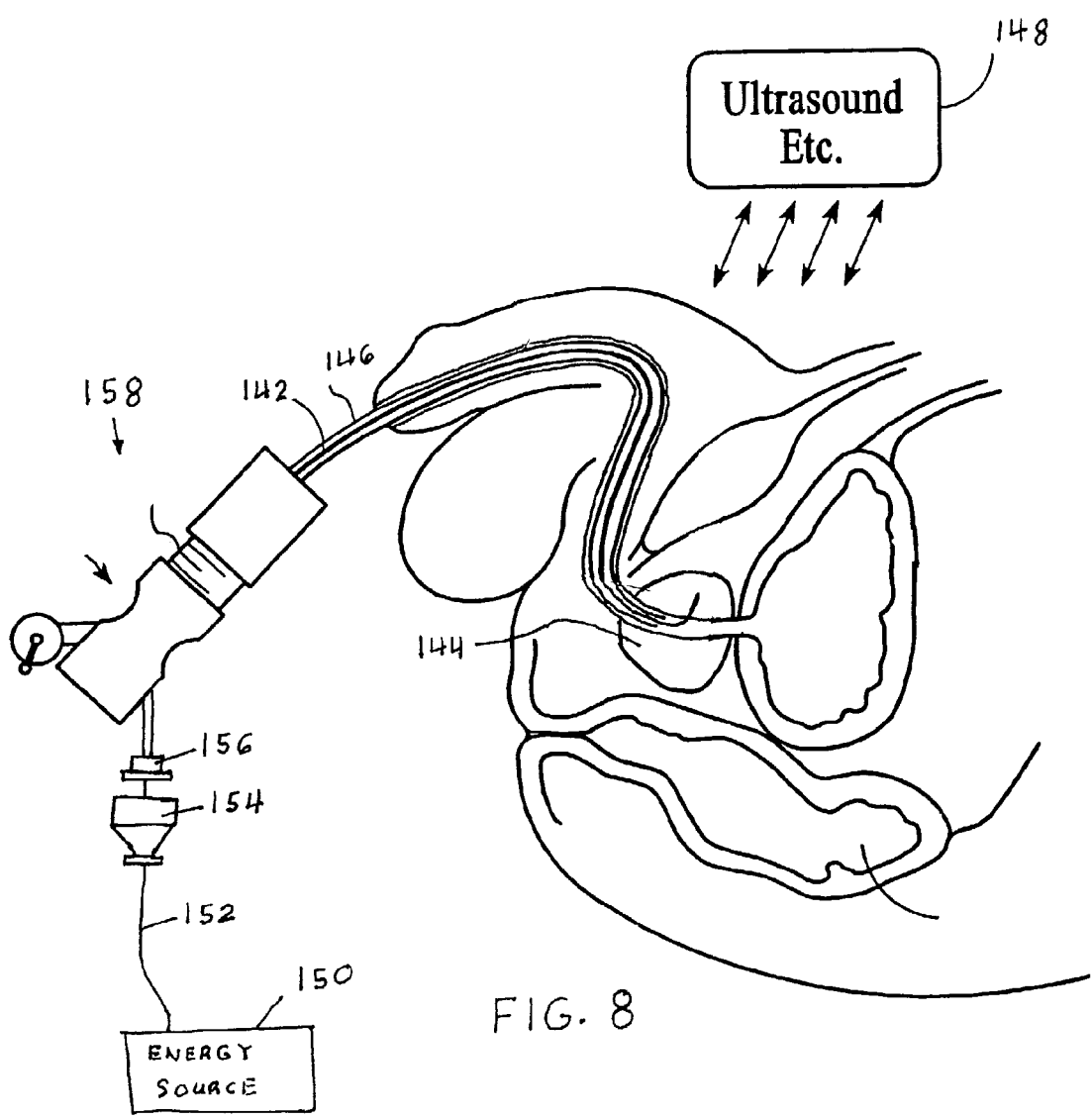
FIG. 8 illustrates use of a flexible probe with non-invasive ultrasound guidance for inserting a needle into a prostate for installation of a transmission device for application of energy.

FIG. 8 illustrates insertion of a needle 142 into a prostate 144 through use of a flexible probe 146 with ultrasound non-invasive imaging guidance 148. As in FIG. 7, energy from a source 150 is transmitted through a transmission device 152 that is fed through the needle 142, and locked into place with securement of a locking cap 154 to a connector 156. Further details of the apparatus 158 in general, and in regarding injection of a treatment substance through the needle is described in reference to FIG. 13 of U.S. patent application Ser. No. 10/193,721.

Figure 9:
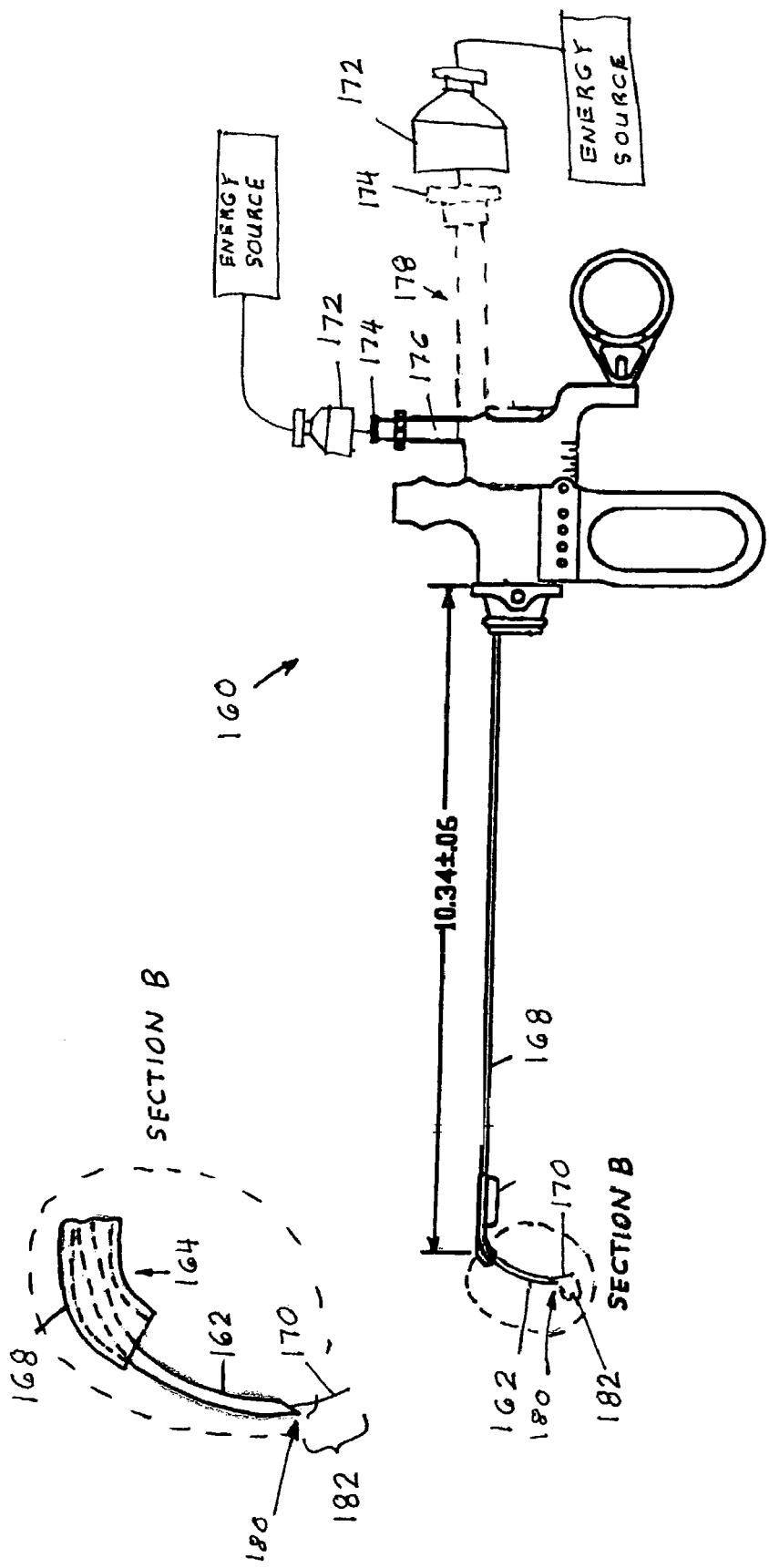
FIG. 9 shows a hysteroscopic, transcervical/transvaginal device configured for inserting a needle in a target tissue for installation of a transmission device through the needle for a localized application of energy.

FIG. 9 is a scaled drawing that shows a cystoscope, hysteroscopic, transcervical/transvaginal injection device 160, with a retractable curved needle 162. A length 164 of the needle guide tube 168 can be curved as shown in more detail in the enlarged section B view, for aiding the extension of the curved needle 162 from the tube 168. The apparatus 160 is similar to the device shown in FIG. 11A of U.S. patent Ser. No. 10/274,497 incorporated herein by reference. As with the other insertion devices described herein and referenced to the related cases, the apparatus 160 is used herein for insertion of a transmission device 170 through the needle 162, and a secured position of device 170 is achieved by way of a locking cap 172, that is similar or identical to cap 32 of FIG. 2, upon connection to a connector 174. For ease of construction and installation of the transmission device 170, the extension 176 in FIG. 9 can alternatively be configured in-line with the guide tube 168 as shown by the dotted lines 178. FIG. 9 illustrates the case where the line 170 is extended beyond the end 180 of the needle 162 as shown more clearly by length 182 in section B.

FIG. 10 is a view of an endoscopic apparatus 184, similar to the apparatus 126 of FIG. 7, except the relative dimensions are more correctly shown for an actual working cystoscopic/ hysteroscopic apparatus, but not drawn for ease of illustration of the various parts. For a detailed description of the working apparatus, refer to FIG. 7 and the corresponding description referenced in the related case. FIG. 10 shows the cystoscopic/ hysteroscopic apparatus 184 as having a long, slender tube 186, which can be either rigid or flexible. The apparatus 184 includes an injection needle 190 which can be curved at 188, or straight as in dashed lines 190. The tube 186 can be inserted, for example through the vagina and cervical canal into a uterus, and the needle can then be deployed into a uterine fibroid interstitially under endoscopic visualization, and/or can be guided by an imaging method as described in reference to FIG. 7 above. For enhanced imaging, the injection needle tip 192 is designed for high echogenecity. The injection needle can also be made from super elastic materials for curved or angular tip articulation.

The transmission device 194 is inserted into the needle 190 through the connector 196, and extended beyond the needle an amount 198 if desired/required for optimum energy distribution. The apparatus of FIG. 10 can in addition be used to inject photosensitizing/energy enhancement substances, agents and dyes as described in U.S. patent application Ser. No. 10/274,497 in reference to FIG. 12 therein.

Figure 11:
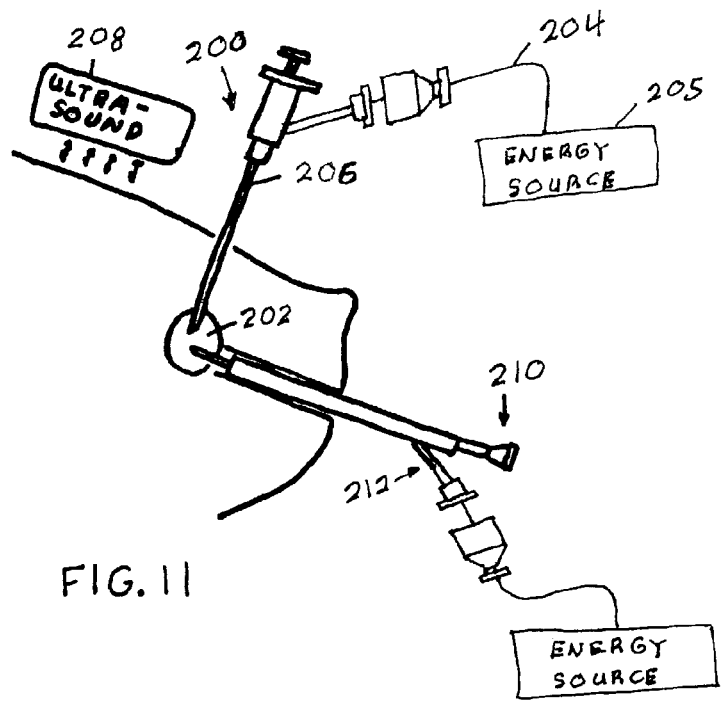
FIG. 11 illustrates percutaneous and endoscopic access to a target tissue in a breast for inserting a needle for installation of a transmission device for localized application of energy.
Figure 12:
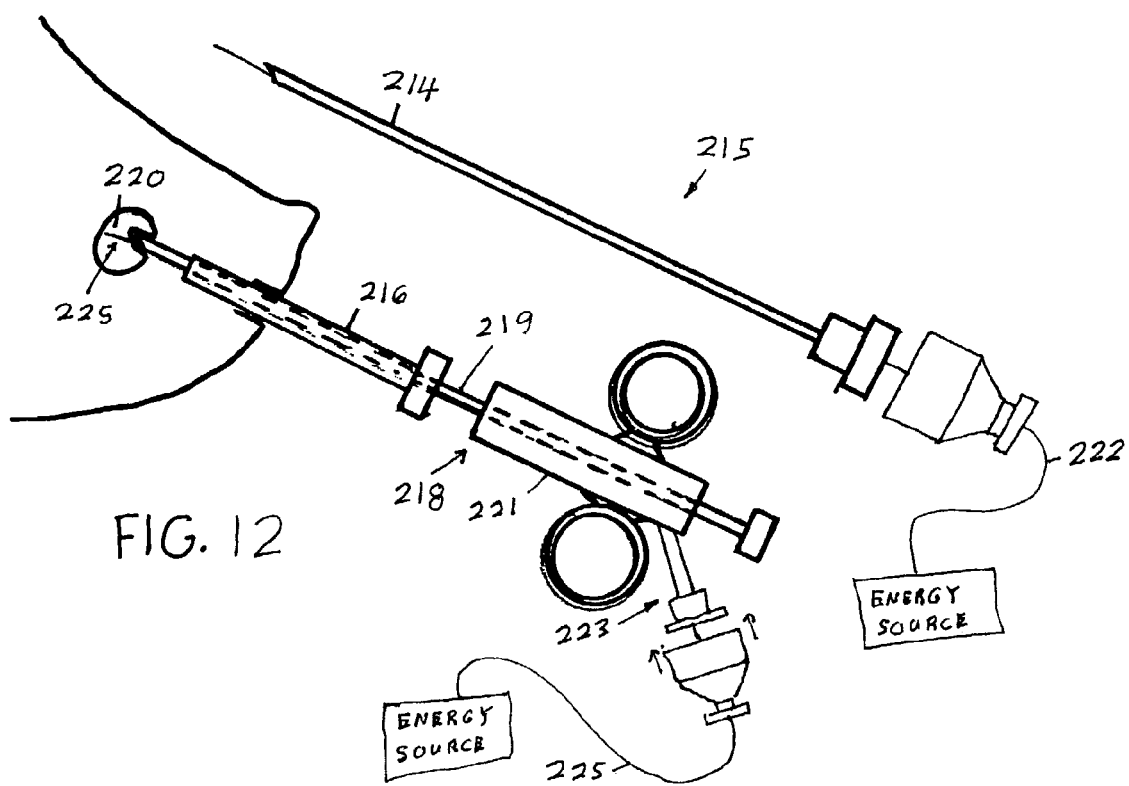
FIG. 12 shows use of a biopsy guide for guiding the insertion of a needle for use in installing a transmission device therethrough for localized treatment of breast tissue.

Application of energy using a transmission device to target tissue in a breast is illustrated if FIGS. 11 and 12. A similar description for injection of photosensitizing/energy enhancement substances, agents and dyes is described in reference to FIGS. 9A and 9B of U.S. patent Ser. No. 10/274,497.

FIG. 11 shows an injection needle/catheter device 200 with a syringe 201 for injection of photosensitizing/energy enhancement substances, agents and dyes, and a needle apparatus 203 for insertion of a transmission device 204 through the needle 206. The needle 206 is inserted percutaneously to the target tissue 202. With the transmission device 204 inserted through the needle 206, energy from source 205 is transmitted to the tissue 202. Alternatively, the needle apparatus 215 shown in FIG. 12 can be used instead of the combination apparatus 200. The needle 206 can be guided in various ways, including use of non-invasive imaging apparatus such as an ultrasound imaging device positioned adjacent the breast, symbolized by block 208 labeled "ultrasound", but can also be another type of imaging device such as CT, MRI, X-Ray, etc. An endoscope 210 apparatus can be used, and inserted through an incision along with a needle apparatus 212. As shown in FIG. 12, a combination device 218 is shown, including a breast biopsy device 221 and a needle extension 223 for introduction of a transmission device 225 through the needle 219. The needle 214 is inserted through an introducer sleeve 216 into target tissue 220, following a biopsy procedure. This method avoids the need for a physician to make an additional puncture for either installing the transmission device, or a needle for injecting photosensitizing/energy enhancement substances, agents and dyes. Alternatively, the needle 214 of device 215 can be inserted through the guide 216 for installation of a transmission device 214, instead of using the combination device 218. Subsequent to initial insertion of the injection needle device (214 or 219) in the breast tumor, the position of the needle and its depth in the target tissue 220 can be confirmed by real time ultrasound imaging. Similar apparatus to FIGS. 11 and 12 are also discussed in U.S. patent Ser. No. 10/274,497 regarding substance injection.

Figure 13:
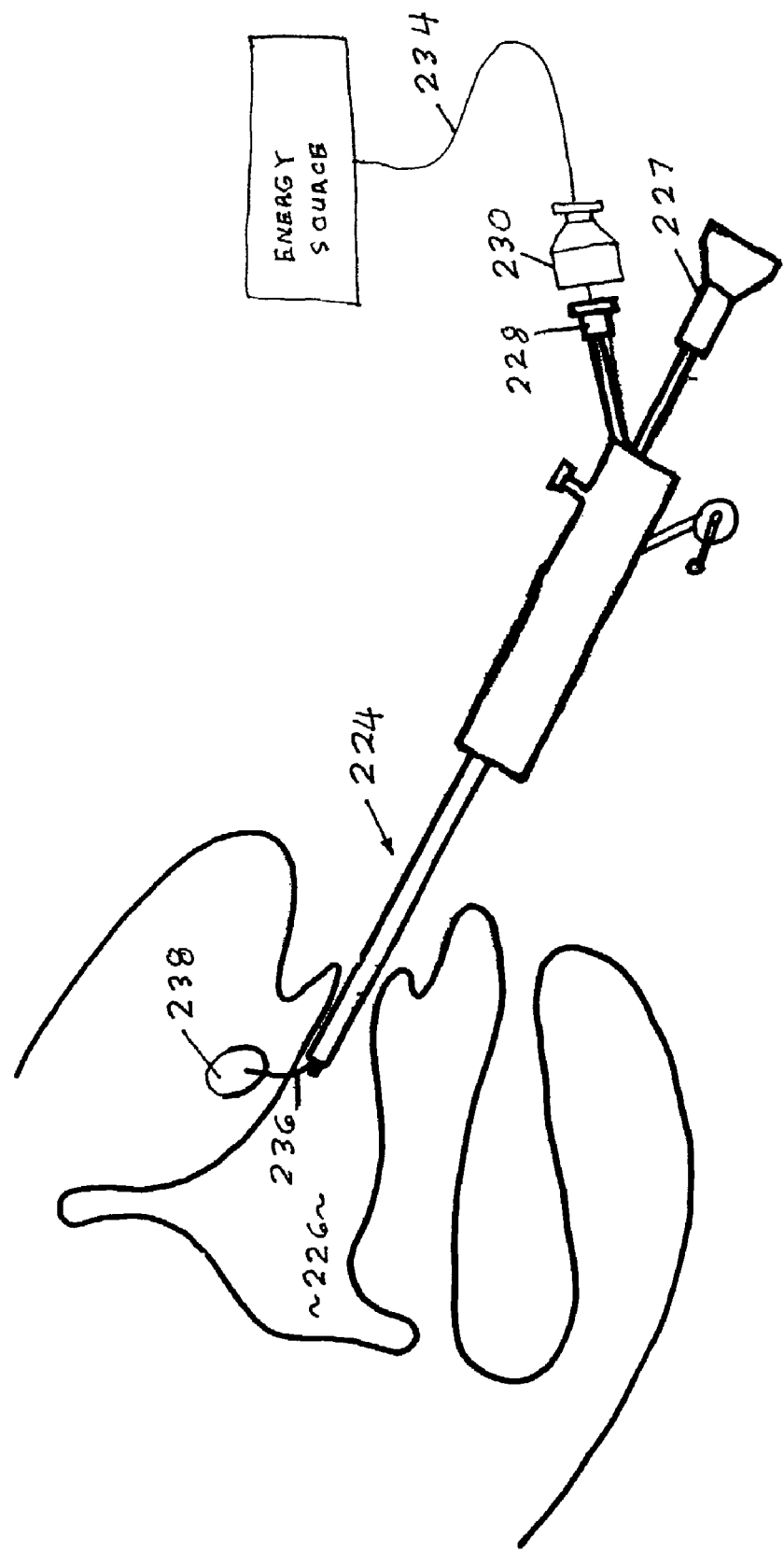
FIG. 13 shows an endoscopic instrument used to access a uterus for inserting a needle into a target tissue for installing a transmission device therethrough for localized application of energy.

FIG. 13 shows an endoscopic/hysteroscopic probe apparatus 224 for accessing the uterus 226. The probe includes an endoscopic viewing device 227 for guidance. FIG. 16 of U.S. patent Ser. No. 10/274,497 describes a similar device for injection of a substance. FIG. 13 shows a connector 228 compatible with a locking cap 230 similar to or identical to cap 32 of FIG. 2. The transmission device 234 is fed through the needle 236 to the target tissue 238.

Transvaginal/transcervical or hysteroscopic access to a uterine fibroid 240 is illustrated in FIG. 14 with a biopsy device 242 having an introducer tube or needle guide 244, using an ultrasound imaging probe 246, or a transvaginal biopsy probe to aid in guiding a biopsy needle 248 to the fibroid 240. The injection delivery needle i.e. transvaginal injection needle device (22-14 ga size) 248 preferably has an echogenic tip 250. The needle 248 is interstitially inserted through the uterine cavity and into the target tissue of the fibroid 240. The device 242 as shown, is again a combination device, similar to that shown in FIG. 12. The needle device 241 is added to the device 242 with a connector 243 and a locking cap 245, all for installation of a transmission device 247 to transmit laser or electromagnetic energy from a source 249 to the target tissue 240. The needle device 248 and similar devices of other configurations for percutaneous functions will be referred to as a percutaneous/interstitial device, as well as a hysteroscopic or transvaginal/transcervical device when used to access the uterine cavity. The end portion 252 of the needle can be straight, curved, angular or articulating to access any part of the fibroid 240 and/or uterine cavity anatomy. The echogenic injection needle tip is visible as a bright white echogenic reflection under ultrasound imaging observation. The needle 248 can be inserted into the uterus using other alternate approaches, such as through a working channel of a transvaginal ultrasound probe or through a working channel of an endoscope, resectoscope or hysteroscope.

FIG. 15 shows an ultrasound probe apparatus 260 with an internal needle guide or biopsy channel 262, and FIG. 16 shows an ultrasound probe 264 with external needle guide apparatus (266, 268) for guiding a needle. The apparatus of FIGS. 15 and 16 can be inserted through a natural body passage/opening such as a rectum, vagina, or vagina and cervix, or through an incision for access to an internal body organ. For example, in FIG. 13, the apparatus 224 can be replaced with the apparatus of either FIG. 15 or 16. In this case, the probe and needle apparatus would be called a endocavity ultrasound imaging probe apparatus/device, or a transvaginal ultrasound imaging probe with an external biopsy needle guide as in FIG. 16, or an internal biopsy needle guide channel as in FIG. 15. Similarly, if the apparatus is used by insertion into the rectum, it would be called a transrectal ultrasound imaging probe device, and if through an incision in the abdomen, it is called a laparoscopic ultrasound imaging probe device. With the apparatus of FIGS. 15 and 16 appropriately dimensioned, it can also be used to access body parts including the urethra, bladder and prostate. In this case, it would be called a cystoscopic or transurethral intraluminal ultrasound imaging device/apparatus.

Referring specifically now to FIG. 15, a combination needle guide and endocavity ultrasound probe apparatus 260 is shown including a functional ultrasound probe portion 270 for imaging, and a channel 262 built into the probe apparatus 260 for guiding a hollow core needle 272, wherein the needle 272 is configured for allowing passage of a transmission device, and alternatively in addition for injecting photosensitizing/energy enhancement substances, agents and dyes.

In operation, the needle 272 is retracted so as to place the tip 274 inside the channel 262. The probe 270 is then inserted into a body passage, such as a rectum. When the operator observes via the ultrasound imaging that the probe is placed in the vicinity of the target tissue to facilitate the insertion of the needle 272 into a target tissue, the needle is thrust forward into the tissue to the desired depth, which can be observed through use of the ultrasound imaging apparatus. With the transmission device installed through the needle, the target tissue can be subjected to laser or electromagnetic energy from a source 287. The needle can also be used to inject photosensitizing/energy enhancement substances, agents and dyes, either before and/or after application of the energy, which is the case also with the other apparatus disclosed herein using a needle to install a transmission device.

FIG. 16 shows a combination needle guide and ultrasound imaging probe apparatus 276, including an ultrasound probe apparatus 264 for imaging, and an attached needle guide apparatus (266, 268) for guiding a hollow core needle 278 along the outside of the probe 264. In commercially available equipment, guide apparatus such as 266 and 268 is provided for guiding a biopsy needle. According to the present invention, this biopsy needle guide apparatus is used to guide the needle 278 configured for installation of a transmission device, and alternatively also for injection of viscous photosensitizing/energy enhancement substances, agents and dyes. The operation of the apparatus 276 involves first placing a protective covering (condom) over the needle guide and probe assembly, with the needle in a withdrawn position behind the tip 280 of the probe 264. Alternatively, the needle tip can be retracted within a structure such as guide support 260, and thereby also preventing the needle tip from penetrating body tissue while the probe and needle assembly 276 is being positioned within a body passage. The probe and needle apparatus 276 is then inserted into a body passage such as a rectum or vagina. With the probe tip 280 in the desired position for inserting the needle 278, the needle 278 is thrust forward, through the protective covering (not shown), and into the target tissue (not shown) to the desired depth, which can be monitored by an ultrasound imaging apparatus including the probe and related instrumentation (not shown). With the transmission device 282 installed, either before or after needle insertion, energy can be transmitted through the device 282. Connector 284 and locking cap 286 are shown in both FIGS. 15 and 16 for securing the device 282 when in place as described in reference to FIG. 2.

Figure 17:
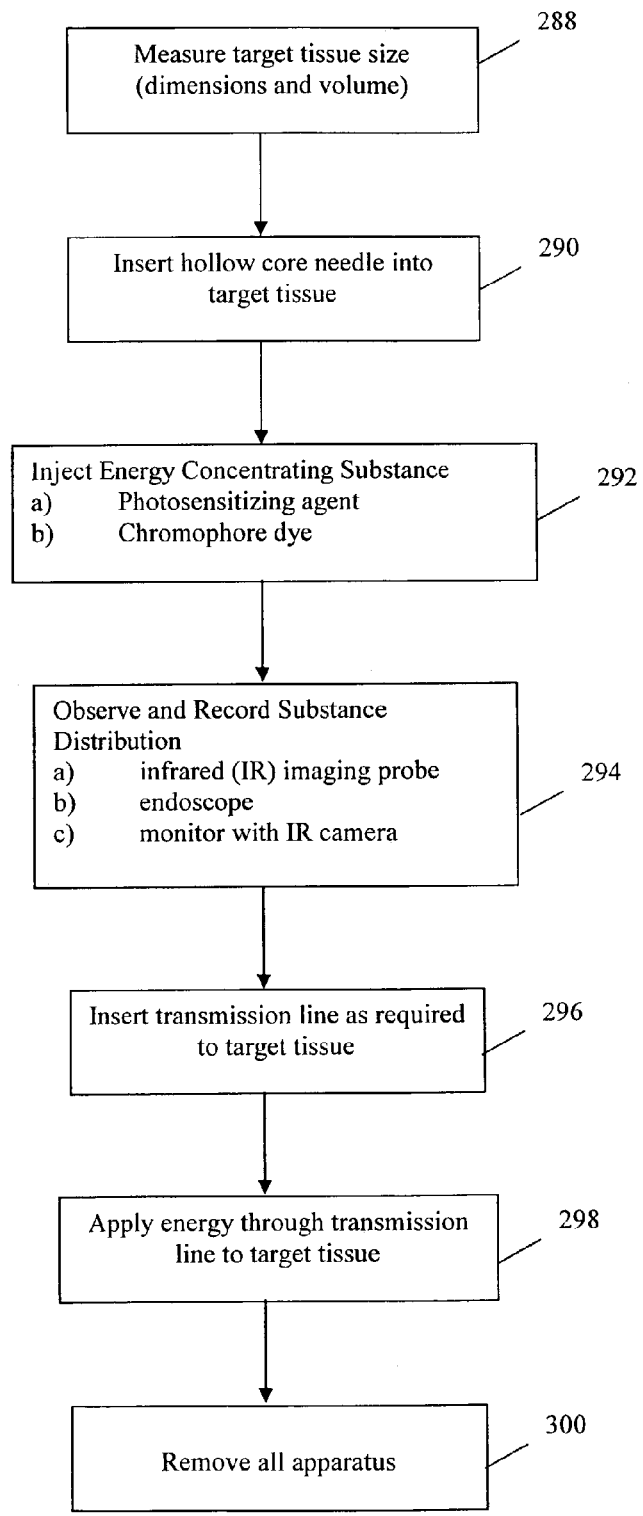
FIG. 17 is a flow chart of a method wherein an energy concentrating substance is injected into a target tissue and then energy is applied.

The present invention of providing a localized application of energy to a target tissue located inside a body is further aided according to the present invention by injecting an energy concentrating/enhancement substance into the target tissue prior to application of the laser or electromagnetic energy. For example, tumor or diseased tissue generally has a higher vascular concentration that accumulates more red blood cells (hemoglobin) than surrounding healthy tissue. Introduction of an energy concentrating agent, such as a photo activating/sensitizing agent and dyes into a tumor results in a higher concentration of the agent being retained in the tumor due to the higher concentration of blood and vascular structure. As a result, applied energy will concentrate in the tumor tissue containing or being saturated in blood containing the photosensitizing agents/dyes. The result of concentrating energy in the tumor is a reduced damage to surrounding healthy tissue. This method is described in reference to FIG. 17. The target tissue size is measured (block 228); and an appropriate quantity of energy concentrating substance or photosensitizing agent/dye dosage is calculated. A hollow core needle is then inserted into the target tissue (block 290) and the appropriate volume of energy concentrating substance or photosensitizing agent/dye is injected (block 292). Substances particularly useful include photosensitizing agents, chromophore dyes or fluorochromes or fluorophore dyes. As an alternative embodiment, the distribution of the energy concentrating substance in the target tissue can be monitored with the aid of an infrared (IR) imaging probe and/or an endoscope, and further alternatively recorded with an IR camera (block 294). The transmission device is then installed through the hollow core needle to the target tissue (block 296), and the required energy is applied i.e. transmitted by an energy source through the transmission device and into the target tissue (block 298), wherein the energy passes most readily into the tissue having received the energy concentrating substance. The apparatus can then be removed (block 300). The energy concentrating substance can include an energy activating agent/substance characterized by the property that when exposed to a particular energy type, such as a particular laser wavelength, it will react by releasing energy or chemically reacting to cause a desired effect on the target tissue. Examples of such substances are heat activated polymers, light activated or pH activated chemical agents/dyes, and radiation and magnetically activated chemical agents, etc.

Energy concentrating substances also include some photosensitizing agents and dyes. Photosensitizing agents are those agents that are activated by light, such as a laser wavelength. The photosensitizing agents and dyes, when exposed to a particular wavelength, absorb the light energy, resulting in heat generation which in the application of the present invention, heats the tissue selectivity in which the agent or dye resides. This process is known as selective photothermolysis, and is included in the present invention in combination with the localized application of laser or electromagnetic energy to an interior body part.

Fluorescence dyes, are evolved from a dye class called the Cyanines, Xathene dyes, phycobiliprotins and Bodipy dyes. Fluorescence can be simply defined as the molecular absorption of light energy (photons) at one wavelength and its re-emission at another, usually longer, wavelength.

Molecules that can absorb light are known as "chromophores," those that both absorb and emit light are know as "fluorochromes" or "fluorophores."

Photosensitizing agents and dyes known as fluorochromes or fluorophores also display florescence, a phenomena wherein when exposed to a certain light wavelength, emit radiation. A photosensitizing agent or dye may respond most strongly with emitting florescence at one specific wavelength or narrow band of wavelength, and absorb energy most strongly upon application of a different wavelength. The present invention utilizes the unique characteristics of fluorophore and fluorochrome dyes to apply peak florescence wavelength to observe the reflected florescence for imaging guidance and to confirm the distribution of the photosensitizing agents, and then apply another specific wavelength for peak absorption of light energy to achieve selective, controlled tissue destruction/necrosis.

The energy concentrating substances defined herein also include what will be termed "energy enhancement" agents. Energy enhancement agents are defined as those substances which increase the absorption of RF, radiation, microwave, ultrasound or laser energy into the target tissue. Examples of energy enhancement agents are: hypertonic saline for RF energy, carbon or dark color pigments or particles and laser dyes for laser energy.

Figure 18:
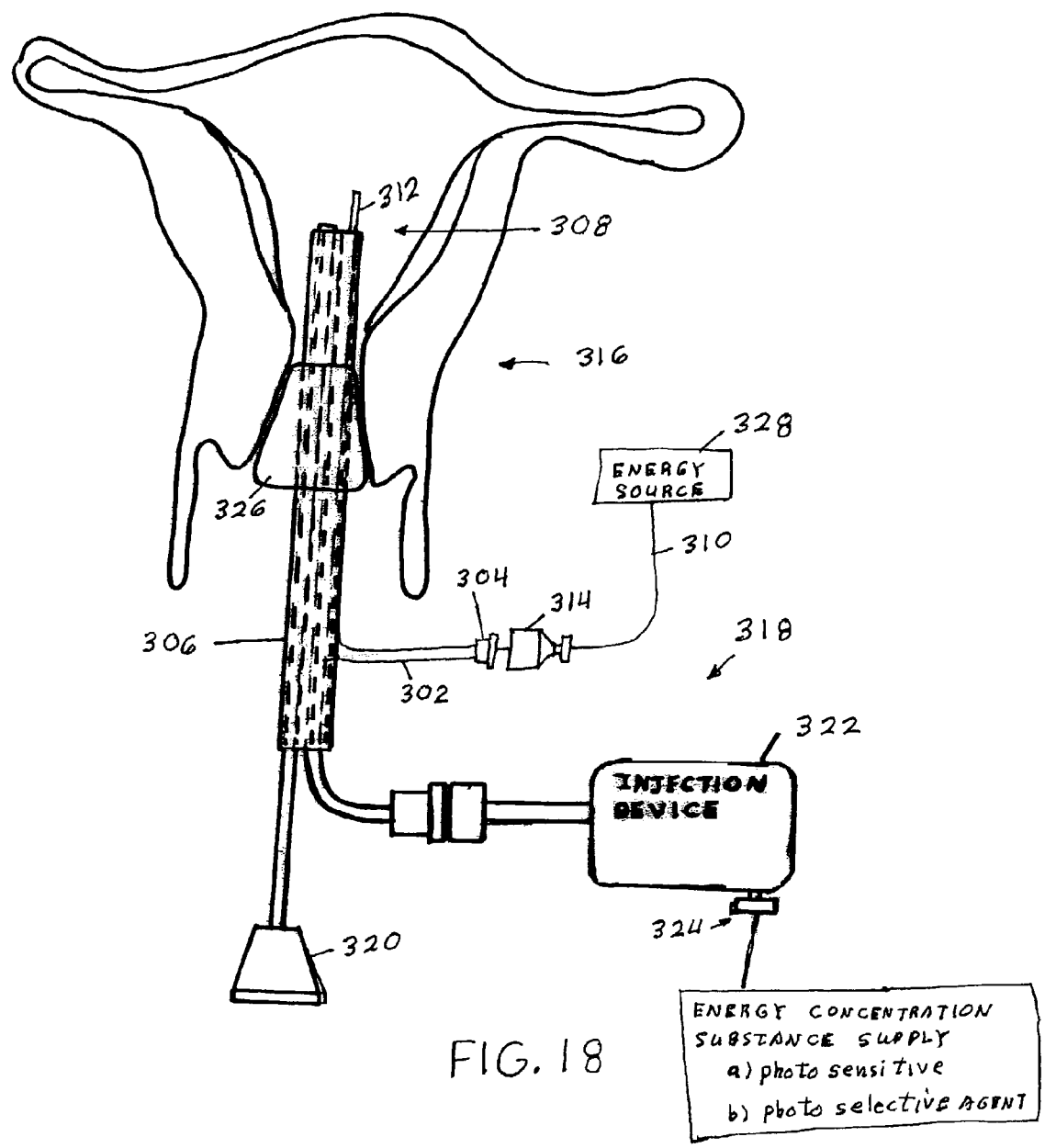
FIG. 18 illustrates application of an energy concentrating substance in a uterus and then applying energy.

U.S. patent Ser. No. 10/274,497 describes a method and apparatus for treating a uterus 316 in reference to FIGS. 19-22 of that application. The present disclosure as shown in FIG. 18 adds the facility to introduce laser or electromagnetic energy. FIG. 18 shows a conduit 302 with a connector 304 attached, the conduit 302 interconnecting with and/or providing passage through probe 306 into the uterine cavity 308. A transmission line 310 is installed through connector 304 and conduit 302 into the cavity 308. Element 312 indicates any of various ways of effecting radiation of the transmitted energy into the cavity 308, such as being merely an extension of the line 310 into the cavity 308, etc. As with the above-described devices, upon installation of the line 310 in position, a locking cap 314 can be secured to connector 304 for locking the line 310 in place, as described fully in reference to FIG. 2. The apparatus 318 includes an endoscope 320 and a substance injection device 322 with input 324. A plug 326 seals the uterus for containing fluid therein. These aspects of the apparatus 318 are more fully discussed in reference to U.S. patent Ser. No. 10/274,497.

The method of use of the apparatus of FIG. 18 for injection of fluid is discussed in detail in U.S. patent Ser. No. 10/274,497, incorporated in the present disclosure by reference. The substance injected into the uterus according to the present invention is an energy concentrating substance with properties as discussed in reference to block 292 of FIG. 17. With the uterine cavity filled with the substance, and with the transmission device 310 installed, the energy source 328 is activated, whereupon the substance in the uterus conducts the energy to the uterine walls for achieving uterine wall ablation.

As discussed above, the energy form sent along the transmission device can be of any type with characteristics selected to allow transmission along a transmission device into an internal body part/target tissue. Energy types, for example include laser, radio frequency (RF), microwave, ultrasound, cryoenergy, X-ray, infrared, UV, gamma, as well as other forms.

Laser energy is of particular interest in achieving localized treatment. The laser energy source can be of any kind, such as Nd:YAG, Nd:Ho, Er:YAG, KTP laser, diode laser, gas pumped lasers including argon laser, krypton laser, dye pumped laser, carbon dioxide laser, ruby laser, excimer laser and other laser energy source.

Figure 19A:
FIG. 19A shows a fiberoptic with a flat tip profile.
Figure 19B:
FIG. 19B shows a fiberoptic with a rounded tip profile.
Figure 19C:
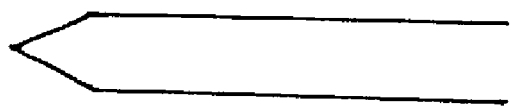
FIG. 19C shows a fiberoptic with a tapered tip profile.
Figure 19D:
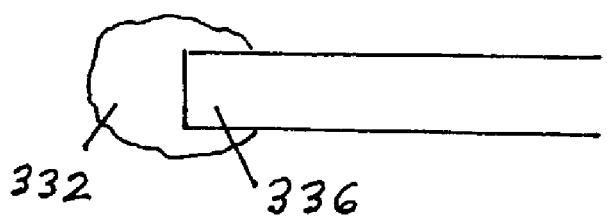
FIG. 19D shows a fiberoptic with application of a coating on the core tip.
Figure 19E:
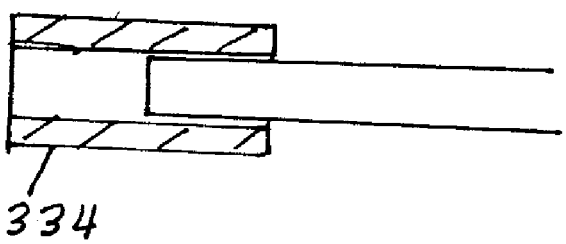
FIG. 19E shows a sleeve over a core tip to create a diffusing tip profile.

A transmission device for laser energy can take different forms. For example, the most popular form is a round rod of constant dielectric and dimension so as to retain the energy as illustrated in FIG. 3B. The energy is confined in the central core in this case. Other forms, such as a metal walled, hollow core tube can also be used if appropriately dimensioned. Example configurations are shown in FIGS. 3B and 3C. When the energy reaches the end of the line, it must radiate into the target tissue. Achieving efficient radiation i.e. reducing of reflections, energy loss and effecting a desired radiation pattern, can be accomplished by configuring the end of the core, and/or applying an attachment/appendage. FIGS. 19A-19E show a variety of fiberoptic core tip/end configurations and profile. FIG. 19A shows a flat surface 330, which can be machined, polished, with a desired surface texture and configuration. FIGS. 19B and 19C illustrate sculpturing the tip for a desired radiation pattern, divergence and optical characteristic. FIG. 19D shows a tip coated with a substance 332 chosen to aid coupling/transmission of the energy into the target tissue. FIG. 19E shows a sleeve 334 designed to achieve a desired energy radiation pattern and diffusion. The sleeve 334 can be designed with a specific dielectric constant, for example, to aid in energy radiation. Glass and polymer materials, for example, can be used. The specific tip configuration can be designed to either diffuse or concentrate/focus the radiated energy according to the specific requirement. This coating or i.e. substance surrounding the tip 336 can be a liquid, solid, gel, suspension or composite.

Figure 20:
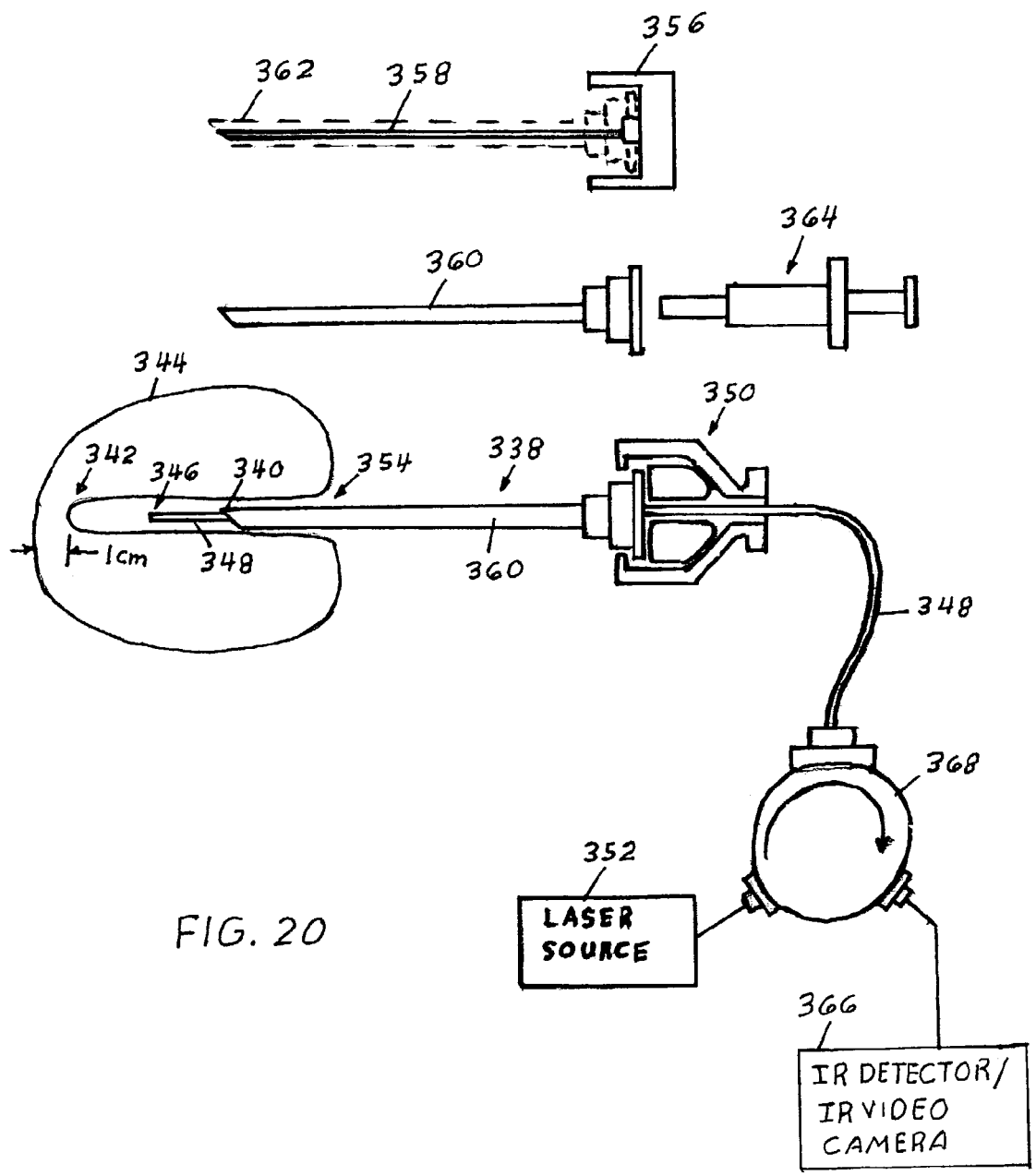
FIG. 20 illustrates additional details of alternate embodiments of the present invention.

A method of treatment of diseases and disorders of body organs including the liver, kidney, bladder, GI tract, rectum, bladder, fibroids, ovary, uterus and other body organs is as follows:

The delivery needle device is inserted either directly into the target tissue of the body organ under unaided visual or manual guidance, or guided using an imaging method such as an endoscope, or ultrasound imaging, CRT, MRI, X-ray or gamma ray imaging devices. The delivery needle device is inserted into the target tissue of the body organ through any of various paths as appropriate for the particular procedure, such as percutaneously, interstitially, transrectally, transperinally, transvesically, transvaginally or any other path of access. The laser fiberoptic waveguide, or other laser transmission device can be inserted into the delivery needle, so that the fiberoptic tip and delivery needle tip are flush. Alternatively, the fiberoptics can be inserted through the needle after the needle is inserted in the body. The position of the fiber is checked by any of various methods such as with depth markings on the laser fiberoptics. Any of the various apparatus as discussed above can be used to aid in inserting the delivery device. For example, the delivery device can be inserted through an ultrasound probe, or biopsy needle guide mounted on an ultrasound imaging probe. For a transurethral approach/path, the delivery needle is inserted into the body organ by way of a working channel of a rigid or flexible cystoscope or resectoscope. Once properly positioned in the target tissue of a body organ, the delivery needle is backed outward so that the laser fiberoptics is exposed from the distal end of the delivery needle, for example at least 1 cm. This is illustrated in the simplified drawing of FIG. 20 wherein the delivery device 338 is simply a needle. The needle tip 340 would initially be inserted to point 342 which is 1 cm away from the outer boundary of an organ 344 or target tissue zone to be ablated. As shown in FIG. 20, the distal tip of the needle 340 has been pulled back from the tip 346 of the optical fiber 348 to expose a desired length of laser fiberoptics. Also as shown, the fiber 348 and needle assembly have been also pulled back from the initial reference point 342 to tip position 346. With the tip 346 initially at 342 and the tip 340 back away from 346 to expose the fiberoptics 348, the fiber 348 and delivery needle assembly 338 are locked together using a locking device such as locking device 350. The laser energy source is then turned on and laser energy is applied to the target tissue for a period of time, for example at least ten (10) seconds. The fiberoptics 348 and delivery device assembly 338 are then pulled back again for a desired distance (such as 1 cm) and the laser source 352 is again activated. This process is continued until the fiber tip 346 is within a prescribed distance (example 1 cm) from the boundary 354 of the organ or target tissue zone 344. The needle tip position can be monitored with ultrasound, CT, MRI, X-ray and other imaging devices. The procedure can then be repeated on another location of the body organ as required to complete treatment. The delivery device can then be removed from the body organ.

FIG. 20 illustrates some additional details regarding alternative embodiments of the present invention. Item 356 is called a stylet. It has a solid core needle 358 that can be inserted inside the hollow core needle 360 to fill the needle 360 during percutaneous insertion of the needle 360 into the target tissue, for the purpose of keeping target tissue from coring or being forced into the tip of the hollow core of the needle 360. Once the needle 360 is in place, such as when the tip 340 is at point 342, the stylet is removed. Dashed outline 362 represents the hollow core needle with the solid needle 358 inside. A syringe 364 is shown to illustrate symbolically that a substance and injectable agents such as described above for any of the purposes discussed can be injected into the target tissue 344 either before, during or after application of laser and/or electromagnetic energy as desired. FIG. 20 also serves to simply illustrate observation of the target tissue using an IR detector, energy detector or IR video camera 366 for observing reflected light/energy from the desired tissue 344. The frequency and wavelength of the laser and energy source 352 can be varied, or the source replaced with one of a different frequency/wavelength for achieving optimum tissue ablation and/or reflectance for observation. Item 368 is simply a circulator illustrating apparatus for directing the transmitted and reflected wavelengths and signals. Alternative apparatus for this purpose will be apparent to those skilled in the art, and these methods and apparatus are included in the spirit of the present invention.

A method of Laser treatment specifically for a prostate for achieving prostate ablation for treatment of BPH and prostate cancer, bladder cancer and lower urinary tract is described as follows:

An appropriate laser wavelength and laser fiberoptic tip and delivery device is selected for treatment of the prostate. A hollow core needle is inserted into the prostate by any of the methods discussed above and in the related cases. For example, this can be done using an access probe guided using an endoscope and/or ultrasound imaging, or CT, MRI, x-ray, or Gamma ray imaging devices. The hollow core needle is inserted into target tissue of the prostate by one of various possible paths including percutaneous, interstitial, transrectal, transperinal, transvesical, or others. A transmission device for laser frequency waves is then inserted into the delivery needle, so that the fiberoptic tip and delivery needle tip are flush. Alternatively, the fiber can be inserted through the needle after the needle has been installed in the target tissue. The position of the fiber can be confirmed with depth markings on the laser fiberoptic transmission line. If access to the prostate is to be achieved transrectally, the delivery needle device can be inserted into the prostate through a transrectal ultrasound probe or biopsy needle guide, mounted on a TRUS probe. For a transurethral approach, the delivery needle is inserted into the prostate through a working channel of a rigid or flexible cystoscope or resectoscope. Once properly positioned into target tissue of the prostate to its full depth as described above in reference to a tissue 344, the delivery needle is pulled outward so that the laser fiberoptic is exposed from the tip of the delivery needle to at least 1 cm in length. The fiberoptics and delivery needle assembly is then locked together using a locking device. The laser energy source is then turned on and laser energy is applied to the target tissue of the prostate for at least ten (10) seconds. The fiber and needle are then backed out an increment such as 1 cm and the laser energy application is repeated. The process is continued until the delivery needle tip is 1 cm away from the boundary of the prostatic capsule. The delivery needle tip position can be monitored with ultrasound imaging. The procedure is repeated on the other side of the prostate lobe and median lobe, if necessary. The delivery device is then removed from the prostate.

Figure 21:
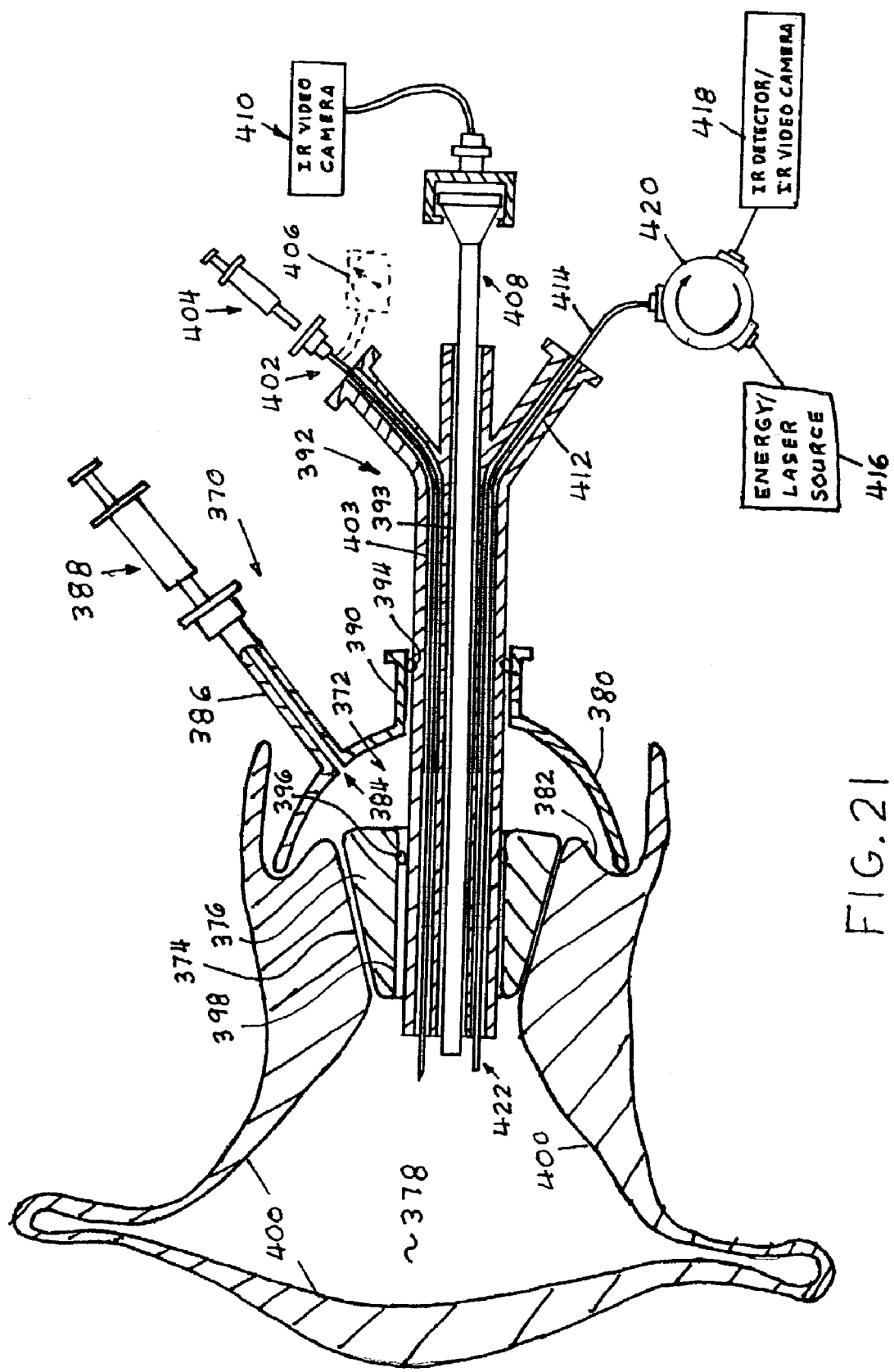
FIG. 21 illustrates apparatus for delivery of energy to a uterus.

FIG. 21 illustrates an apparatus 370 for providing a degree of vacuum to the cervical area in the vagina canal 372 and for the purpose of causing the external (atmospheric) pressure to force and thereby seal the cervix 374 against a plug 376 in order to retain an injected energy enhancement/concentrating substance and photosensitizing agents/dyes in the uterine cavity 378. The apparatus 370 includes a suction cup shaped device 380 for sealing against tissue 382 of the vagina and/or cervix. A vacuum port 384 leads via a vacuum line 386 to a vacuum pump 388 illustrated symbolically as a hand held vacuum type of device similar to a syringe, but which can be any kind of vacuum pump apparatus designed so as to be capable of providing the required vacuum. The apparatus 370 has a tube 390 extending from the suction cup device 380, through which an injection and endoscopic/imaging apparatus 392 can pass. The tube 390 and/or apparatus 392 in one embodiment are of dimensions so as to provide an adequate vacuum seal between them to retain a sufficient vacuum in the vaginal area 372 in the suction cup device 380. Alternatively, an O-ring 394 can be used to achieve the necessary seal. Similarly, an O-ring 396 can be placed between the apparatus 392 and the plug bore 398 for providing the required seal to retain the vacuum in the vaginal cavity 372, and the photosensitizing/energy enhancement substance in the uterine cavity 378. Alternatively, the sealing plug 376 can be designed from rubber, silicone, kryton, latex or other materials with self sealing properties.

The sealing apparatus 370 and plug 376 and details of the installation and operation, including monitoring pressure of an injected substance in the cavity 378, as well as other details are discussed in U.S. patent application Ser. No. 10/274,436 incorporated herein in its entirety by reference. The apparatus as illustrated in FIG. 21 of the present application provides for application of laser or electromagnetic energy to the uterine cavity 378 for causing ablation of the uterine wall 400. The process of achieving this includes an injection of an energy conducting/enhancement substance into the cavity 378. As illustrated, the injection is accomplished through a substance injection apparatus 402 inserted through a first channel 403. The injectable substance is supplied by a substance source 404. The apparatus 402 can, for example be a hollow core needle, or other delivery device such as the apparatus illustrated in FIG. 22 of U.S. patent application Ser. No. 10/274, 436. The apparatus 402 may also alternatively include an injectable substance pressure monitoring device 406 symbolically representing apparatus such as that described in Ser. No. 10/274,436.

The apparatus 392 as shown includes an endoscopic apparatus 408 inserted through a second channel 393 for viewing inside the cavity 378 with an infrared (IR) imaging device/video camera 410 attached, for viewing and alternatively recording. A third channel 412 is for inserting a transmission device 414 for application of energy to the cavity 378. FIG. 21 shows an energy source 416 for generating and transmitting the energy to the transmission device 414.

Alternatively, a reflectance wavelength/signal detector/camera device 418 can also be connected, such as an infrared detector or camera. A circulator apparatus 420 is shown to symbolize methods known to those skilled in the art for directing transmission and reception effectively.

In operation, the equipment as shown is installed, and a substance for conducting laser and electromagnetic energy from the radiating end 422 of the transmission device 414 to the uterine wall 400 is injected into the cavity 378 by way of apparatus 402. This process, as well as the process of tissue ablation can be monitored using the IR cameras 410 and 418 and/or imaging device such as ultrasound apparatus described in FIG. 22 items 310 and 308 of U.S. patent application Ser. No. 10/274,436. With the uterine cavity filled with the required substance, the energy source 416 is activated, resulting in controlled ablation of the endometrial uterine wall 400, the condition being monitored as explained above.

As discussed in reference to FIG. 7B, a channel such as 403, and apparatus such as 402 can be used in cooperation with an irrigating fluid source, which can be symbolized as item 404, for irrigation of the uterus. The channel 403 and apparatus 402 also are used herein to symbolize/demonstrate apparatus for evacuation of substance from the cavity 378. Item 404 in this case would symbolically illustrate a fluid source or pump. Various methods and apparatus for irrigating and aspirating the uterus will be apparent to those skilled in the art, and these are to be included in the spirit of the present invention in combination with the methods of applying energy described herein.

Figure 22:
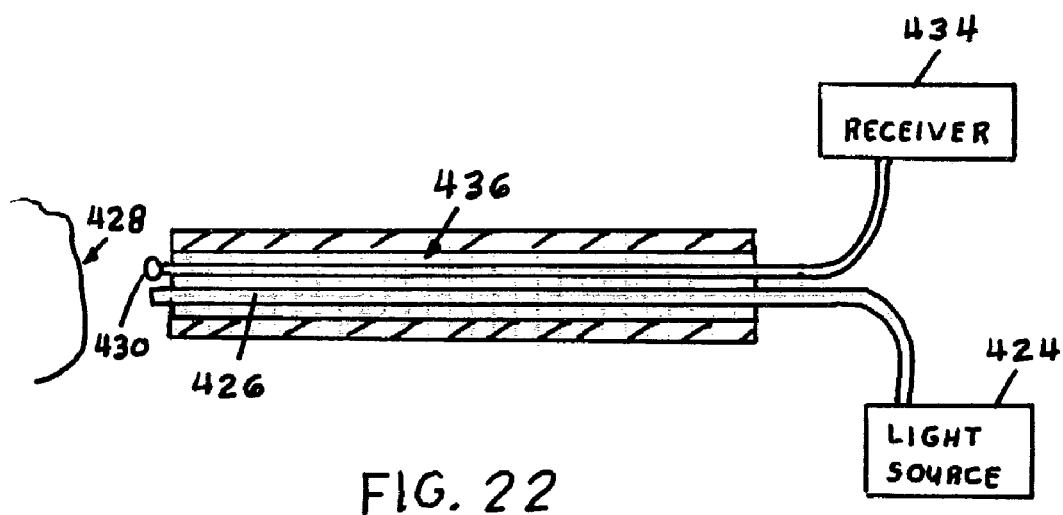
FIG. 22 illustrates use of fiber optics and a CCD for viewing.

FIG. 22 illustrates use of a light source 424 for transmitting light through a light delivery device 426 (such as fiber, etc.) to a target tissue 428. FIG. 22 illustrates use of a charge coupled device (CCD) 430 for detecting the light reflected from the tissue 428, and a transmission device 432 to carry the detected light to a receiver 434. FIG. 22 shows a channel 436 for insertion of the light transmission device 426 and CCD 430. The channel 436 can be in a separate probe or a channel in any of various probe types, including but not limited to those described herein.

It is known that tumors have a different tissue density, vascular structure, and cellular composition than normal cells, and will reflect a different reflectance wavelength/color than healthy tissue. Selecting a particular light wavelength/frequency makes it easier to distinguish diseased tissue from healthy tissue. The apparatus of FIG. 22 is provided for this purpose, in addition to the apparatus as described in reference to FIGS. 20 and 21 for viewing tissue. The use of a fluorescence substance is also included for viewing tissue reflectance by applying a select wavelength of light to a tissue having been injected with a photosensitizing agent and dye as discussed above. Examples of photosensitizing agents and pH sensitive dyes that exhibit this property are Fluorescein dye, Indocyanine green dye, Indigo Carmen dye, Rhodamine dye, India ink, Bodipy dye, Coumarine, Xanthene dyes, phycobiliprotines, Texas red dye, Oregon green dye, Nile blue dye, Cascade blue dye and other laser dyes.

Another method and apparatus for observing tissue effects according to the present invention in combination with application of energy and energy concentrating substances and fluorescence substances is the use of ultrasound. The above discussion includes the use of ultrasound imaging for guidance in placement of the delivery device/apparatus. Ultrasound imaging is also provided according to the present invention for viewing the effects on target tissue from the application of energy. Ultrasound energy provides real time monitoring of blood flow, fluid content and tissue necrosis. As the target tissue is destroyed, the blood flow and density of tissue changes, and this change in density and blood flow movement can be observed with ultrasound imaging using the apparatus described above in the incorporated cases.

The present invention also includes monitoring of temperature, pH and humidity in the target area. This can be done by inserting a thermocouple and/or pH, humidity sensor. For purposes of illustration, the sensor 430 in FIG. 22 can symbolically represent a temperature, pH or humidity sensor.

The above embodiments of the present invention have been given as examples, illustrative of the principles of the present invention. Variations of the method and apparatus will be apparent to those skilled in the art upon reading the present disclosure. These variations are to be included in the spirit of the present invention.

What is claimed is:

1. A method of treating a body part comprising the steps of:
    (a) inserting a hollow core needle into a target tissue in a body;
    (b) injecting an energy enhancement substance for conduction of energy selected from the group consisting of electrical, radio frequency, microwave, and ultrasound energy and for converting said energy to heat into said target tissue through said needle;
    (c) inserting a transmission device through said needle;
    (d) transmitting energy to said target tissue through said transmission device to cause controlled necrosis of said target tissue; and
    (e) observing an area of target tissue for guiding energy delivery by:
        (i) injecting a photosensitizing agent/chromophore/fluorophore dye having a florescence characteristic;
        (ii) applying a selective light wavelength for activating said florescence; and
        (iii) observing said florescence with an infrared (IR) camera and imaging device.

2. A method as recited in claim 1 wherein said energy enhancement substance is an energy activating agent in a form selected from the group consisting of liquid, solid, semi-solid, suspension, conjugate, and viscous form.

3. A method for treating a prostate and lower urinary tract of a human body comprising:
    (a) inserting an energy delivery apparatus including a hollow core needle into a prostatic target tissue via an approach selected from the group consisting of transurethral, transperineal, transrectal and transvesical, wherein said energy delivery apparatus delivers energy selected from the group consisting of electrical, radio frequency, microwave, and ultrasound energy;
    (b) injecting at least one energy enhancement substance into said target tissue through said delivery apparatus, wherein said substance is for conducting said energy and converting said energy to heat;
    (c) inserting a transmission device through said needle;
    (d) monitoring the energy delivery apparatus using an imaging device selected from the group consisting of transrectal ultrasound imaging device, endoscope, cystoscope, and resectoscope,
    (e) injecting the prostatic target tissue with a photosensitizing agent/chromophore/fluorophore dye having a fluorescence characteristic and applying a selective light wavelength for activating said fluorescence;
    (f) observing said fluorescence with an infrared (IR) camera and imaging device; and
    (g) applying said energy to said target tissue through said delivery apparatus.

* * * * *